US012276663B2

(12) United States Patent
Phillips et al.

(10) Patent No.: US 12,276,663 B2
(45) Date of Patent: Apr. 15, 2025

(54) DETECTION OF HUMAN LEUKOCYTE ANTIGEN-A*32:01 IN CONNECTION WITH DETERMINING DRUG REACTION WITH EOSINOPHILIA AND SYSTEMIC SYMPTOMS (DRESS) AND METHODS OF TREATING BACTERIAL INFECTION IN A SUBJECT WITH VANCOMYCIN-INDUCED DRESS

(71) Applicant: VANDERBILT UNIVERSITY, Nashville, TN (US)

(72) Inventors: Elizabeth Phillips, Nashville, TN (US); Simon Mallal, Nashville, TN (US); Katherine Konvinse, Nashville, TN (US); Abha Chopra, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 781 days.

(21) Appl. No.: 17/427,887

(22) PCT Filed: Feb. 14, 2020

(86) PCT No.: PCT/US2020/018420
§ 371 (c)(1),
(2) Date: Aug. 2, 2021

(87) PCT Pub. No.: WO2020/168282
PCT Pub. Date: Aug. 20, 2020

(65) Prior Publication Data
US 2022/0107316 A1 Apr. 7, 2022

Related U.S. Application Data

(60) Provisional application No. 62/805,717, filed on Feb. 14, 2019.

(51) Int. Cl.
G01N 33/569 (2006.01)
(52) U.S. Cl.
CPC ......... G01N 33/56977 (2013.01); G01N 2333/70539 (2013.01); G01N 2800/24 (2013.01)
(58) Field of Classification Search
CPC ... G01N 33/56977; G01N 2333/70539; G01N 2800/24
See application file for complete search history.

(56) References Cited

U.S. PATENT DOCUMENTS 7,858,319 B2   12/2010   Hetherington et al.
2012/0135418 A1   5/2012   Kim et al.

FOREIGN PATENT DOCUMENTS

WO   WO 2012/083240 A2   6/2012
WO   WO 2018/232316 A1   12/2018

OTHER PUBLICATIONS

Littlehales, Emma et al. "Vancomycin-Induced DRESS Syndrome: An Important Concern in Orthopedic Surgery." Case reports in orthopedics vol. 2018 1439073. Jun. 24, 2018, doi: 10.1155/2018/1439073 (Year: 2018).*
Wolfson, Anna R et al. "Drug Reaction with Eosinophilia and Systemic Symptoms (DRESS) Syndrome Identified in the Electronic Health Record Allergy Module." The journal of allergy and clinical immunology. In practice vol. 7,2 (2019): 633-640. doi: 10.1016/j.jaip.2018.08.013 (Year: 2019).*
Cheng, Changming et al. "Detection of rare point mutation via allele-specific amplification in emulsion PCR." BMB reports vol. 46,5 (2013): 270-5. doi:10.5483/bmbrep.2013.46.5.155 (Year: 2013).*
Konvinse et al. "HLA-A*32:01 Is strongly associated with vancomycin-induced drug reaction with eosinophllia and systemic symptoms," The Journal of Allergy and Clinical Immunology, Feb. 16, 2019 (Feb. 16, 2019), vol. 144, Iss. 1, pp. 183-192.
Park et al. "HLA Allele Frequencies in 5802 Koreans: Varied Allele Types Associated with SJS/TEN According to Culprit Drugs," Yonsei Medical Journal, Nov. 30, 2015 (Nov. 30, 2019), vol. 57, Iss. 1, pp. 118-126.
Roy et al. "Vancomycin-Induced Drug Reaction with Eosinophilia and Systemic Symptoms (DRESS) Syndrome Masquerading as Elusive Sepsis," Case Reports in Immunology, Apr. 10, 2019 (Apr. 10, 2019), vol. 2019, pp. 1-5.
Alfirevic, et al., Drug Induced Hypersensitivity and the HLA Complex, Pharmaceuticals 2011, 4, 69-90.
Konvinse KC, Trubiano JA, Pavlos R, James I, Shaffer CM, Bejan CA, Pilkinton MA, Rosenbach M, Zwerner JP, Williams KB, Jack Bourke J, Martinez P, Rwandamuriye F, Chopra A, Watson M, Mallal SA, Redwood A, White KD, Phillips EJ: HLA-A*32:01 Is Strongly Associated with Vancomycin-Induced Drug Reaction with Eosinophilia and Systemic Symptoms. J Allergy Clin Immunol 2019.
Nakkam N, Trubiano J, Gibson A, Phillips EJ. Considerations for cross-reactivity between vancomycin and other glycopeptides. J Allergy Clin Immunol Pract. Aug. 2021;9(8):3233.
Nakkam N, Gibson A, Mouhtouris E, Konvinse KC, Holmes NE, Chua KY, Deshpande P, Li D, Ostrov DA, Trubiano J, Phillips EJ. Cross-reactivity between vancomycin, teicoplanin, and telavancin in patients with HLA-A?32:01-positive vancomycin-induced DRESS sharing an HLA class II haplotype. J Allergy Clin Immunol. Jan. 2021;147(1):403-405.

(Continued)

Primary Examiner — Elizabeth C. Kemmerer
Assistant Examiner — Mckenzie A Dunn
(74) Attorney, Agent, or Firm — Stites & Harbison PLLC; Mandy Wilson Decker

(57) ABSTRACT

Methods of detecting a human leukocyte antigen (HLA)-A*32:01 allele in a subject as disclosed are useful, for example, to determine whether the subject is at risk for developing or has vancomycin-induced drug reaction with eosinophilia and systemic symptoms (DRESS). Methods of treating bacterial infection in a subject with vancomycin-induced DRESS are also disclosed.

19 Claims, 16 Drawing Sheets

Specification includes a Sequence Listing.

(56) References Cited

OTHER PUBLICATIONS

Rwandamuriye FX, Chopra A, Konvinse KC, Choo L, Trubiano JA, Shaffer CM, Watson M, Mallal SA, Phillips EJ. A Rapid Allele-Specific Assay for HLA-A*32:01 to Identify Patients at Risk for Vancomycin-Induced Drug Reaction with Eosinophilia and Systemic Symptoms. J Mol Diagn. Sep. 2019;21(5):782-789.

* cited by examiner

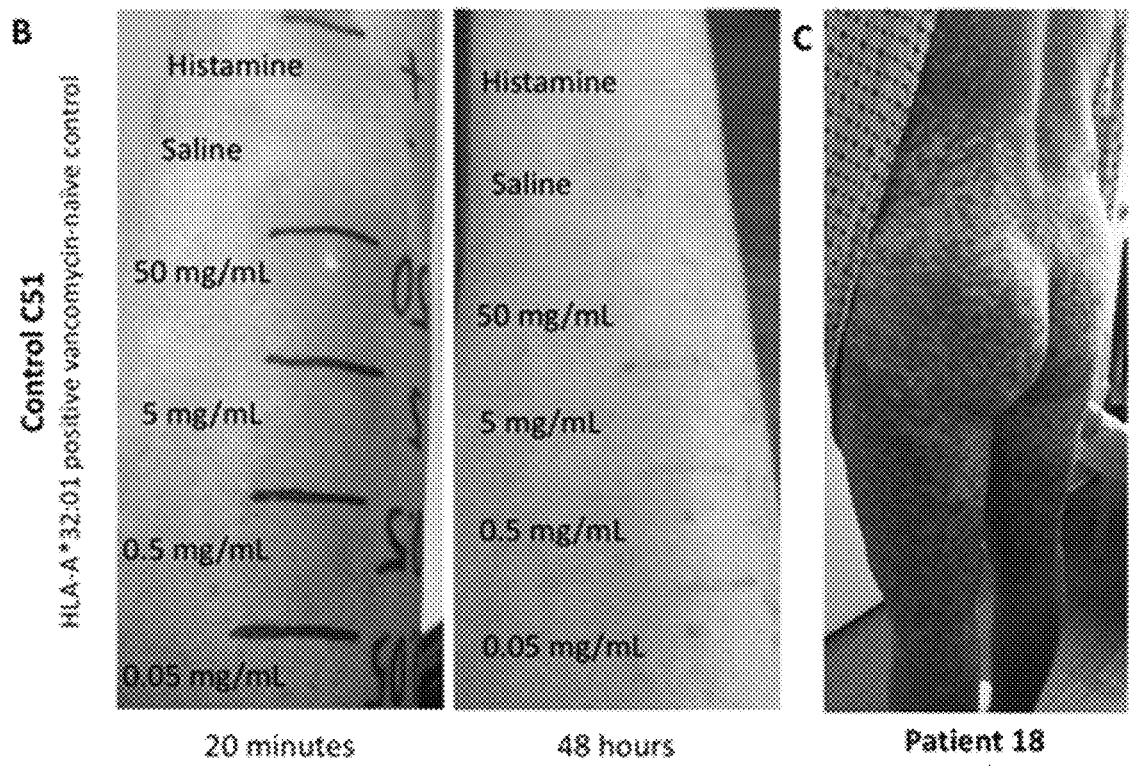
FIG. 3B
FIG. 3C
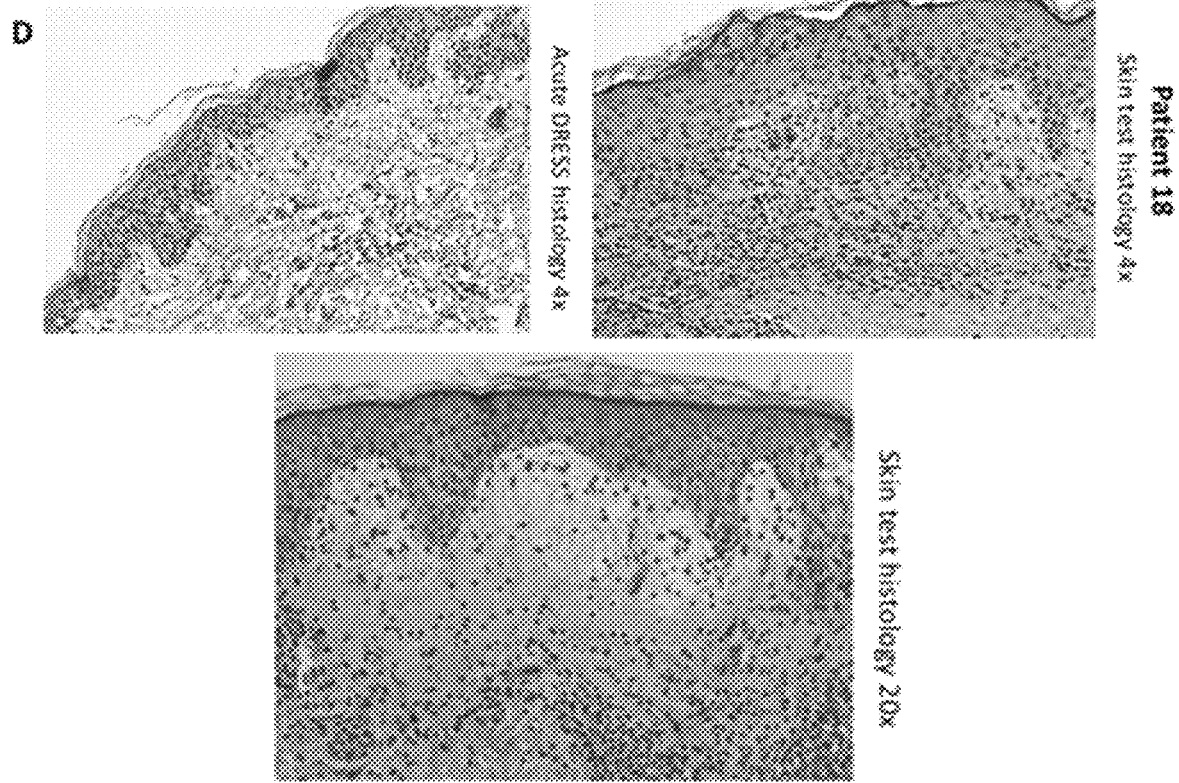
FIG. 3D

|  | HLA-A*32:01 Positive (n=137) | HLA-A*32:01 Negative (n=137) | p-value |
|---|---|---|---|
| Age (years) | | | |
| Mean (SD) | 52.6 (21.0) | 47.7 (22.3) | 0.061 |
| Longest treatment length (days) | | | |
| Mean (SD) | 17.3 (13.5) | 20.0 (15.0) | 0.12 |
| Sex n (%) | | | |
| Female | 50 (36.5%) | 61 (44.5%) | |
| Male | 87 (63.5%) | 76 (55.5%) | 0.22 |
| Race n (%) | | | |
| European American | 125 (91.2%) | 120 (87.6%) | |
| Other | 12 (8.8%) | 17 (12.4%) | 0.43 |
| Adverse Reaction n (%) | | | |
| Yes | 20 (14.6%) | 12 (8.8%) | |
| No | 117 (85.4%) | 125 (91.2%) | 0.19 |
| Possible or definite DRESS n (%) | | | |
| Yes | 13 (9.5%) | 0 (0%) | |
| No | 124 (90.5%) | 137 (100%) | 0.00018 |

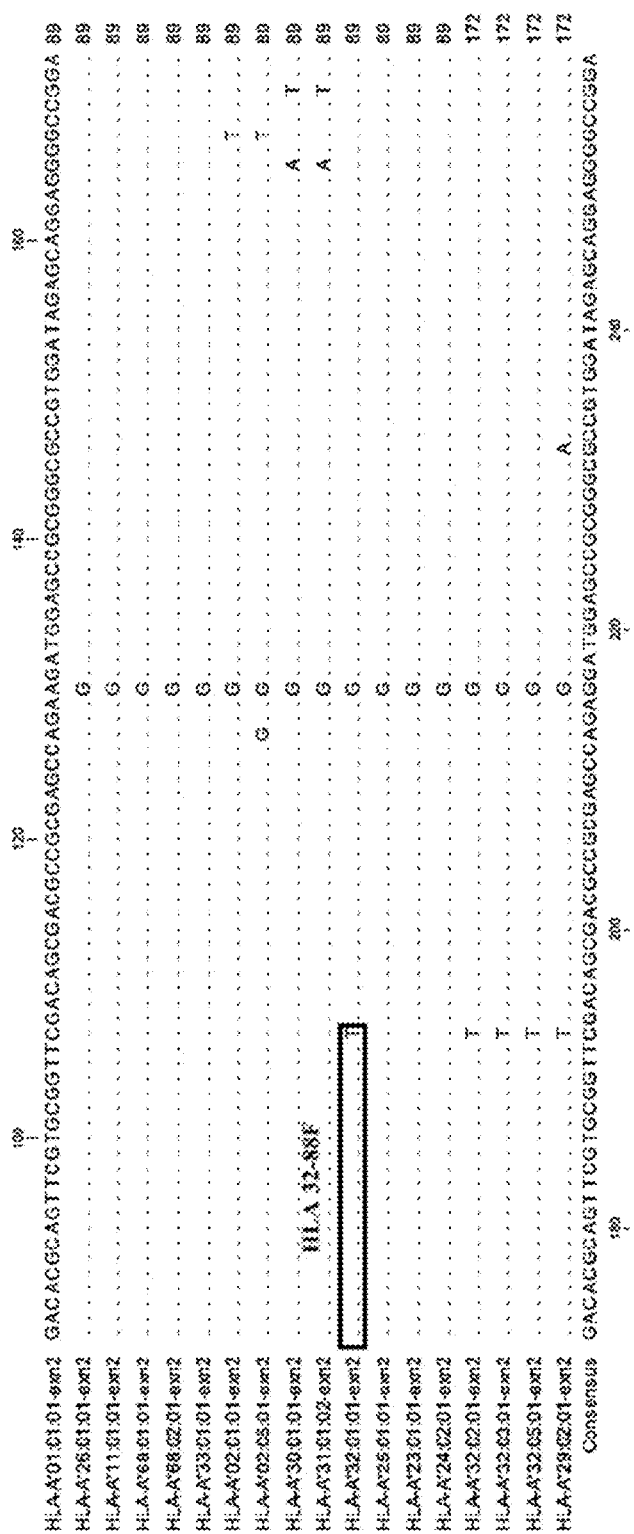
FIG. 8, con't

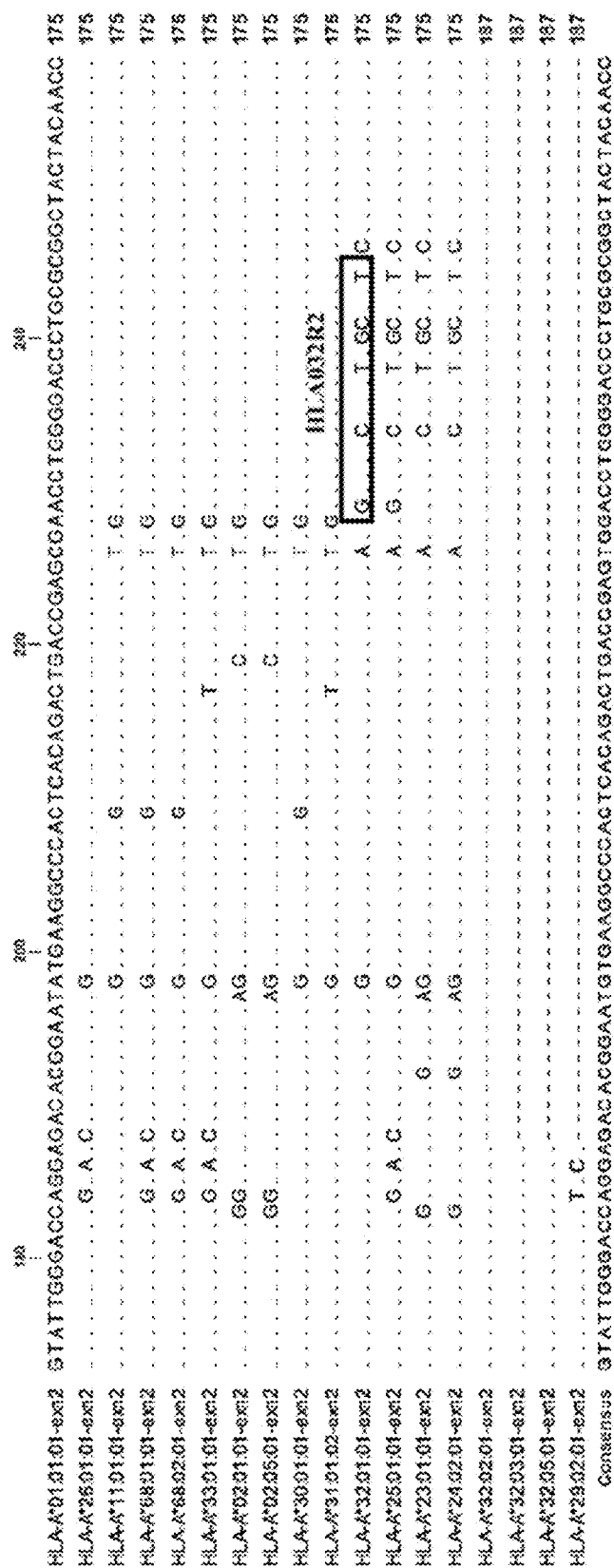
FIG. 8, con't

DETECTION OF HUMAN LEUKOCYTE ANTIGEN-A*32:01 IN CONNECTION WITH DETERMINING DRUG REACTION WITH EOSINOPHILIA AND SYSTEMIC SYMPTOMS (DRESS) AND METHODS OF TREATING BACTERIAL INFECTION IN A SUBJECT WITH VANCOMYCIN-INDUCED DRESS

RELATED APPLICATIONS

This application claims priority from U.S. Provisional Application Ser. No. 62/805,717 filed Feb. 14, 2019, the entire disclosure of which is incorporated herein by this reference.

GOVERNMENT INTEREST

This invention was made with government support under Grant Numbers AI131780, AI136815, AI139021, GM115305, and HG010863, awarded by the National Institutes of Health. The government has certain rights in the invention.

REFERENCE TO AN ELECTRONIC SEQUENCE LISTING

The contents of the electronic sequence listing (Phillips VU 19098WO_ST25.txt; Size: 1152 bytes; and Date of Creation: Feb. 14, 2020) is herein incorporated by reference in its entirety.

INTRODUCTION

Vancomycin is a widely used antibiotic of global importance for the treatment of serious, deep-seated, antibiotic-resistant Gram-positive infections such as methicillin-resistant *Staphylococcus aureus* which require prolonged treatment courses. Vancomycin is associated with infusional pruritus and rash ("red man syndrome") which is managed by slow infusion and anti-histamines. However, vancomycin is also a very common antibiotic-related cause of a life-threatening delayed T-cell mediated reaction known as drug reaction with eosinophilia and systemic symptoms (DRESS)[1].

DRESS, otherwise known as drug-induced hypersensitivity syndrome, typically develops 2-8 weeks after drug initiation and presents with fever, a widespread rash, facial edema, white cell abnormalities, and involvement of internal organs such as the liver, kidneys, heart and lungs[2]. The mortality of DRESS is as high as 10% and long-term morbidity such as autoimmune disease has been described up to 4 years following acute disease[3,4]. When DRESS develops in the setting of combination antibiotics, all treatment is stopped and future exposure to all concurrently-dosed antibiotics is contraindicated due to the associated risks of morbidity and mortality if DRESS reoccurs.

Vancomycin is a glycopeptide antibiotic. All glycopeptide antibiotics contain a heptapeptide core structure and they inhibit bacterial cell wall synthesis by preventing transglycosylation and transpeptidation through binding to the C-terminal D-alanyl-D-alanine (D-Ala-D-Ala) and inhibiting the terminal phase of peptidoglycan synthesis.[50] Because of the similarities in chemical structure of glycopeptide antibiotics, cross-reactivity should be considered when treating patients who have had a previous hypersensitivity reaction to vancomycin or other drugs in the same class.

Published case reports suggest a risk for cross-reactivity between vancomycin and teicoplanin.[51, 52, 53] However, this remains controversial as some patients presenting with teicoplanin-induced DRESS showed subsequent tolerability to vancomycin,[52] and patients with teicoplanin-induced DRESS confirmed by positive intradermal skin test had a negative skin test to vancomycin.[54] A recent report described a patient with an immediate reaction to vancomycin who showed subsequent tolerability to dalbavancin.[55] However with this report, it is unclear that this represented a true immune-mediated reactions since vancomycin causes non-IgE mediated mast cell activation which with rapid infusion of vancomycin can be severe and true anaphylaxis is very uncommon.[56] There is currently no data on immunological cross-reactivity amongst structure sharing glycopeptide and lipoglycopeptide antibiotics with regards to DRESS which is the most common severe delayed reaction associated with vancomycin.

The ability to more definitively diagnose DRESS associated with vancomycin may allow patients not only to avoid the current and future risk of vancomycin exposure, or exposure to other drugs in the same class, but also to continue or resume therapy with other falsely implicated antibiotics.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a method of detecting a human leukocyte antigen (HLA)-A*32:01 allele in a subject, which involves obtaining a biological sample from the subject, and detecting whether HLA-A*32:01 is present in the sample to determine whether the subject is at risk for developing or has vancomycin-induced drug reaction with eosinophilia and systemic symptoms (DRESS) when HLA-A*32:01 is present in the sample.

The presently-disclosed subject matter also includes a method of identifying risk of developing vancomycin-induced DRESS in a subject, which involves obtaining a biological sample from the subject, and detecting whether HLA-A*32:01 is present. In some embodiments in the sample using a primer mix containing one or both of HLA 32-88F (SEQ ID NO: 1) and HLA032R2 (SEQ ID NO: 2).

In some embodiments of the method, the subject has a bacterial infection. For example, in some embodiments, the bacteria is an antibiotic-resistant gram-positive bacteria. In some embodiments, the bacteria is methicillin-resistant *Staphylococcus aureus*.

In some embodiments of the method, the biological sample is from a subject suspected of having DRESS. In some embodiments, the subject is receiving combination antibiotic treatment that includes vancomycin. In some embodiments, the subject is diagnosed as having vancomycin-induced DRESS when the presence of HLA-A*32:01 in the sample is detected. In this regard, in some embodiments, the method also involves administering to the diagnosed subject an antibiotic treatment that excludes vancomycin.

In some embodiments of the method, the biological sample is from a subject in need of treatment with an antibiotic. In this regard, in some embodiments the method also includes identifying the subject as being at risk for developing vancomycin DRESS when the presence of HLA-A*32:01 in the sample is detected. In some embodiments, the method involves administering an antibiotic that is not vancomycin to the identified subject. In some embodiments, the method involves administering an antibiotic that is not a glycopeptide antibiotic to the identified subject. In some embodiments, the method involves administering an antibiotic that is not vancomycin, teicoplanin, or telavancin to the identified subject. In some embodiments, the method involves administering dalbavancin to the identified subject.

In some embodiments of the method, sequenced-based typing is conducted to determine whether HLA-A*32:01 is present in the sample. In some embodiments of the method, SNP2HLA is used to determine whether HLA-A*32:01 is present in the sample. Some embodiments of the method also involve using an IFN-γ Enzyme-Linked ImmuneSpot assay. In some embodiments of the method, a polymerase chain reaction assay is used to determine whether HLA-A*32:01 is present in the sample. In this regard, some embodiments of the method involve using allele-specific polymerase chain reaction (AS-PCR). Some embodiments of the method involve using quantitative polymerase chain reaction (qPCR).

In some embodiments of the method involving use of a polymerase chain reaction assay, a primer mix containing a primer specific for HLA-A*32 allele. In some embodiments, the primer specific for HLA-A*32 is HLA 32-88F (SEQ ID NO: 1). In some embodiments, the method also involves using a second primer specific for HLA-A*32 that is HLA032R2 (SEQ ID NO: 2). In some embodiments, the method also involves using a primer targeting a housekeeping gene. In some embodiments, the housekeeping gene is galactosylceramidase (GALC). In some embodiments, the primer targeting GALC is GALc-F (SEQ ID NO: 3). In some embodiments, the method also involves using a second primer targeting GALC that is GALc-R (SEQ ID NO: 4).

The presently-disclosed subject matter also includes a kit comprising a primer specific for HLA-A*32. In some embodiments, the kit includes HLA-A*32 is HLA 32-88F (SEQ ID NO: 1) and HLA-A*32 that is HLA032R2 (SEQ ID NO: 2). In some embodiments, the kit also includes GALc-F (SEQ ID NO: 3) and GALc-R (SEQ ID NO: 4).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 1B. IFN-γ release ELISpot results after 18-hour stimulation with vancomycin at concentrations of 250 µg/mL (grey) or 500 µg/mL (black) using peripheral blood mononuclear cells from vancomycin DRESS patients. Controls included cells from vancomycin-naïve, HLA-A*32:01 positive healthy donors (n=3) including the son of case patient 18 and the vancomycin skin test negative control C51, an HLA-A*32:01 positive individual tolerant of 4 weeks of vancomycin (n=1), patients who had developed a non-DRESS immune-mediated adverse reaction to vancomycin (n=5) and non-HLA matched healthy donors (n=4). Means of the replicates are plotted. In patients with multiple blood draws at time points distant from the reaction, ELISpot results from the first blood draw are plotted. 12/14 (85.7%) DRESS cases had a positive vancomycin ELISpot compared to none of the controls ($p=0.005$ (DRESS vs. HLA-A-32:01 positive controls), $p=0.002$ (DRESS vs. non-DRESS ADRs), $p=0.005$ (DRESS vs. non-HLA matched healthy donors)). Positive results are those above the dotted line intersecting the y-axis at 50 SFU/million cells. Differences in proportion of positive responses between groups were assessed using Fisher's exact tests. Patient and control peripheral blood mononuclear cells (PBMCs) were also stimulated with vancomycin at concentrations of 5 µg/mL and 50 µg/mL and exhibited a dose-dependent response (data not shown). The figure was generated using GraphPad Prism 7.0a Macintosh Version, GraphPad Software, La Jolla California USA, graphpad.com. Legend: Vanc, vancomycin; HLA, human leukocyte antigen; DRESS, drug reaction with eosinophilia and systemic symptoms; ELISpot, Enzyme-Linked ImmunoSpot assay; ns, not significant; SFU, spot-forming units; IM-ADR, immune-mediated adverse drug reaction.

FIG. 3A-3E. Vancomycin skin testing, acute DRESS skin eruption and skin biopsy histology. FIGS. 3A and B. Vancomycin intradermal testing (IDT) results in patient 18 approximately 6.5 months after developing vancomycin DRESS and control C51, an HLA-A*32:01 positive, vancomycin-naïve healthy donor. IDT was performed on the volar forearm of the skin with 0.02 mL of vancomycin at concentrations of 0.05, 0.5, 5 and 50 mg/mL. The positive histamine and negative saline controls worked as expected. Vancomycin produced a strong immediate histamine response at 20 minutes in both control C51 and patient 18, but only patient 18 with a history of HLA-A*32:01 positive DRESS developed a concentration dependent induration of the skin at 48 hours at the 0.5, 5 and 50 mg/ml concentrations. FIG. 3C. A representative example of the skin eruption from patient 18 during acute vancomycin DRESS. She had a diffuse morbilliform exanthema with facial involvement and facial edema (not shown). FIG. 3D. Hematoxylin and eosin staining of punch biopsies of skin from patient 18. Acute DRESS histology from a skin biopsy taken three days following onset of symptoms (upper panel) and skin test histology from the 5 mg/ml vancomycin positive intradermal skin test at 48 hours (lower panels) demonstrate papillary dermal edema, epidermal spongiosis and a dense lymphocytic infiltrate. The skin test histology mirrors the results from the acute biopsy. FIG. 3E. Immunohistochemistry of T-cell subsets from acute DRESS and positive skin test biopsies from patient 18. Healthy skin is shown for comparison (upper panel). There was no discernable difference in the distribution of CD4 and CD8 positive cells in the dermal infiltrate between the acute (middle panel) and skin test (lower panel) biopsies. The number of intraepidermal CD8 positive cells was substantially higher in the acute biopsy. There was no appreciable exocytosis of CD4 T cells in the acute biopsy or CD4 or CD8 T cells in the biopsy from vancomycin IDT. Notably, dermal FOXP3+, regulatory T cells were present in the skin test biopsy, but absent in the acute biopsy. Additionally, patient 18 had negative IDT to levofloxacin (not shown) and was successfully rechallenged with levofloxacin, a drug that, at the time of reaction, was administered with vancomycin.

FIG. 5B. Vancomycin DRESS patients 9, 18 and 20 had multiple blood draws at time points distant from the initial reaction with repeat positive results. Counting from the start of DRESS symptoms, sample time points were at one month, two months, seven months and four years for patient 9, seven months and ten months for patient 18, twelve days and three months for patient 20, and two months, three months and six months for patient 21. Blood from time point 2 on patient 9 was drawn during steroid treatment, which likely dampened the ELISpot response. Patient 21 does not carry HLA-A*32:01 and had a persistently negative vancomycin ELISpot. Means of the replicates are plotted. Positive results are those above the dotted line intersecting the y-axis at 50 SFU/million cells. The figure was generated using GraphPad Prism 7.0a Macintosh Version, GraphPad Software, La Jolla California USA, graphpad.com. Legend: Patient ID, patient identification; SFU, spot-forming units.

FIG. 7B. The maximal treatment periods were similar for HLA-A*32:01 negative patients and HLA-A*32:01 positive patients who did not develop DRESS.

FIG. 9A: HLA-A*32:01-positive (n=5) and non-HLA-A*32 (n=5) samples were amplified by polymerase chain reaction (PCR) using the following validated primers: HLA 32-88F forward primer and HLA032R2 reverse primer to amplify the HLA-A*32 allele. GALC-F and GALC-R primers were used to amplify the internal control housekeeping gene in a multiplexed reaction. PCR products were run on a 1% agarose gel containing 0.2 µg/ml ethidium bromide at 115V for 30 minutes. The gel was visualized by a transilluminator (ChemiDoc XRS+, Bio-Rad, Australia). HLA-A*32:01 positive samples showed two bands of 157-bp (HLA-A*32:01 product) and 352-bp (GALC product). Non-HLA-A*32 samples showed only one band of 352-bp (GALC product). FIG. 9B: Tm peaks for the HLA-A*32:01 allele were clearly separate from the and GALC Tm peak following melt curve analysis. FIGS. 9C and 9D: Melting peaks and curves for a subset of the 458 samples tested in a real-time PCR with Power Up SYBR Green are shown. HLA-A*32:01-positive samples (n=30) showed double Tm peaks at 88.5° C.±0.0° C. (mean standard error of the mean; range: 88.50° C.-88.50° C.) for the HLA-A*32:01 allele and 76.05° C. 0.03° C. (mean±standard error of the mean; range: 76.00° C.-76.50° C.) for GALC. Non-HLA-A*32 allele samples showed a single Tm peak at 76.07° C.±0.01° C. (mean±standard error of the mean; range 75.50° C.-76.50° C.) for GALC.

BRIEF DESCRIPTION OF THE SEQUENCE LISTING

Figures 1A, 1B:
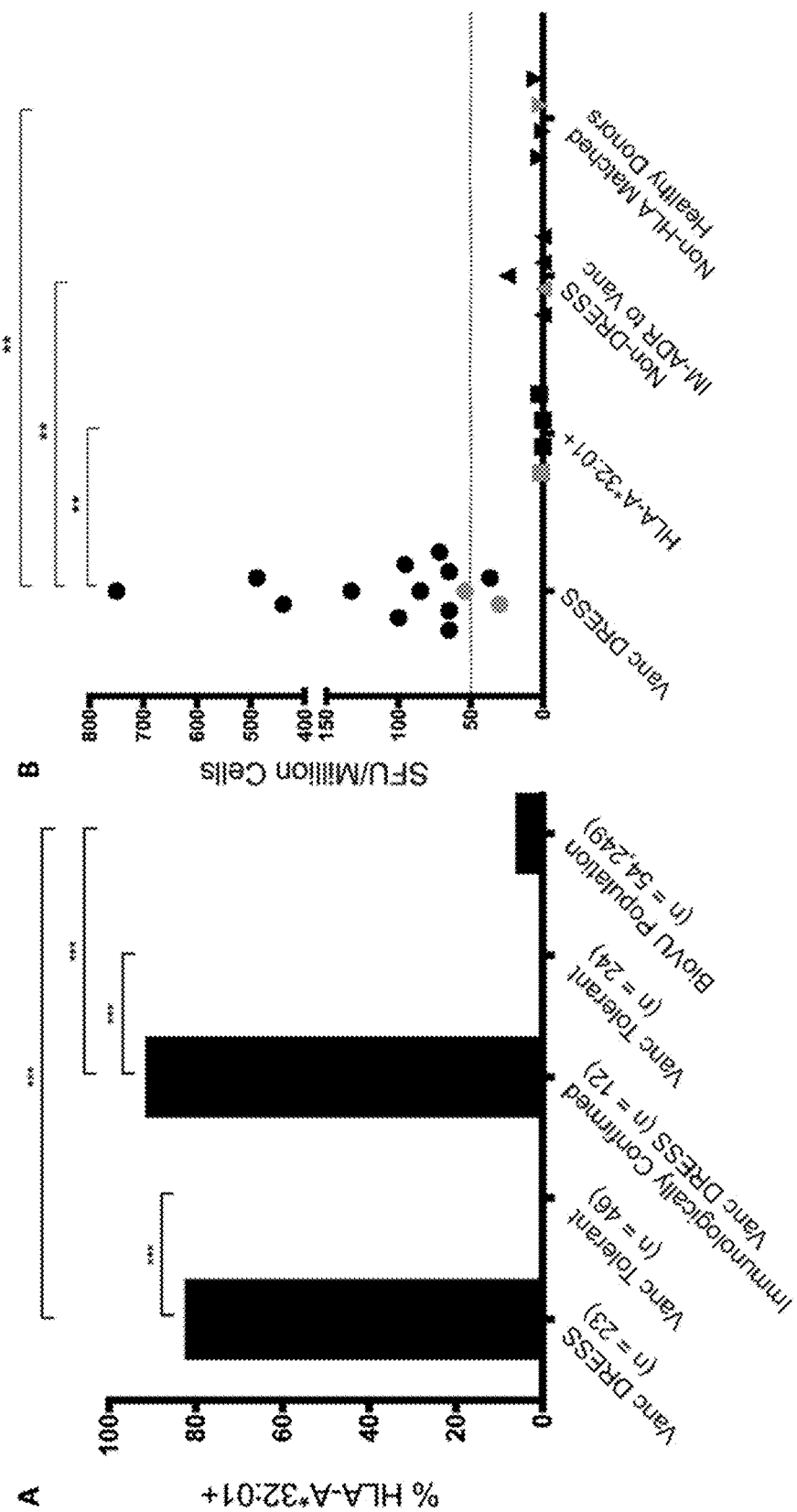
FIG. 1A-1B. HLA-A*32:01 is strongly associated with vancomycin DRESS. 19/23 (83%) DRESS cases carried HLA-A*32:01 compared with 0/46 (0%) of the matched vancomycin tolerant controls ($p=1\times10^{-8}$, conditional logistic). If analyses is restricted to immunologically confirmed cases, then 11/12 (92%) vancomycin ELISpot positive patients carried HLA-A*32:01 compared with 0/24 (0%) of the BioVU matched controls ($p=9\times10^{-7}$, conditional logistic). HLA-A*32:01 carriage in all identified vancomycin DRESS cases and immunologically confirmed cases was also very significantly overrepresented compared to HLA-A*32:01 carriage in the entire BioVU cohort ($p=2\times10^{-16}$ and $p=2=7\times10^{-13}$ respectively, exact binomial tests). There was no significant difference in HLA-A*32:01 carriage between the vancomycin tolerant populations and the BioVU cohort ($p=0.12$ for all controls, $p=0.40$ for controls matched to immunologically confirmed cases, exact binomial tests). Additionally, there was no significant difference in HLA-A*32:01 carriage between the immunologically confirmed vancomycin DRESS cases and those that were not immunologically confirmed ($p=0.32$, Fisher's exact test). All analyses shown included Bonferroni correction for multiple comparisons.

SEQ ID NO: 1 is HLA 32-88F (GACGACACGCAGTTCGTGCGGTT+T, LNA).
SEQ ID NO: 2 is HLA-A*32 that is HLA032R2 (GAGCGCGATCCGCAGGC, STD).
SEQ ID NO: 3 is GALC-F: TTACCCAGAGCCCTATCGTTCT.
SEQ ID NO: 4 is GALC-R: GTCTGCCCATCACCACCTATT.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is based, in part, on the inventors' discovery that carriage of the HLA-A*32:01 allele is strongly associated with the development of vancomycin DRESS, and can be used to help preempt and implicate vancomycin as the casual drug for DRESS to improve the safety and efficacy of antibiotic treatment.

The presently-disclosed subject matter is also based, in part, on the inventors' discovery and design of a unique assay for improved accuracy, ease, and cost associated with HLA typing. Conventional HLA typing is done by serological or sequence-specific typing methods such as PCR amplification with use of sequence-specific oligonucleotide probes (SSO) or sequence-based typing (SBT) techniques. Standard serological approaches lack specificity, as commercially-available monoclonal antibodies cross-react with different HLA alleles[36]. HLA typing using SSO sometimes results in low resolution products that are unable to resolve some HLA alleles[37]. HLA typing by SBT is able to resolve HLA alleles with high resolution but is comparatively expensive, requires specialized DNA sequencing equipment and a skilled operator for analysis, and is time-consuming to prepare and analyze results. Disclosed herein is a simple and fast PCR assay that uses allele-specific polymerase chain reaction (AS-PCR). This AS-PCR method is less susceptible to laboratory and analysis errors, and is easier and less expensive to implement as a clinical test for presence and absence of carriage of HLA-A*32:01.

The presently-disclosed subject matter is also based, in part, on the inventors' discovery that immunological cross-reactivity is demonstratable between vancomycin, teicoplanin and telavancin in patients with clinically and immunologically defined HLA-A*32:01 restricted vancomycin DRESS, while dalbavancin, a derivative of teicoplanin, showed little to no cross-reactivity highlighting it as the safest alternate glycopeptide.

The presently-disclosed subject matter includes methods and kits for use in detecting human leukocyte antigen-A*32: 01 (HLA-A*32:01) in connection with diagnosing and/or predicting risk of vancomycin-induced drug reaction with eosinophilia and systemic symptoms (DRESS). The presently-disclosed subject matter further includes methods for identifying risk of developing and/or diagnosing vancomycin DRESS in a subject. The presently-disclosed subject matter further includes methods for identifying risk of developing and/or diagnosing vancomycin DRESS in a subject and treating the subject for a bacterial infection. In some embodiments, the method involves obtaining a biological sample from the subject and detecting whether HLA-A*32:01 is present in the sample.

As will be recognized by the skilled artisan, "predicting a risk" of a condition does not refer to the ability to predict the course or outcome with 100% accuracy, or even that a given course or outcome is predictably more or less likely to occur based on the presence, absence or levels of a panel of markers. Instead, the skilled artisan will understand that the term "predicting a risk" refers to identifying a probability that a certain course or outcome will occur; that is, that a course or outcome is more likely to occur in a subject exhibiting a given condition, when compared to those individuals not exhibiting the condition.

In some embodiments the subject has a bacterial infection. Such a bacterial infection can include, for example, an infection with an antibiotic-resistant gram-positive bacteria or methicillin-resistant *Staphylococcus aureus*. Such infections are commonly treated with vancomycin and, as will be appreciated by the skilled artisan, it is particularly useful to predict or diagnose vancomycin DRESS prior to initiation of a treatment or combination treatment that employs vancomycin, so that alternate antibiotic treatment options can be identified and used.

In some embodiments, the biological sample being tested is from a subject in need of treatment with an antibiotic. For example, the subject could be one who has been diagnosed with a bacterial infection, but who has not yet received antibiotic treatment. In this regard, a sample from the subject could be tested and the subject could be identified as being at risk of developing vancomycin-induced DRESS when the presence of HLA-A*32:01 in the sample is detected. With such a diagnosis, an antibiotic treatment can be selected to exclude vancomycin. However, if HLA-A*32:01 is not detected in the sample, vancomycin can be considered as part of the antibiotic treatment strategy.

In some embodiments, the biological sample is from a subject suspected of having DRESS. For example, the subject could be receiving treatment, such as a combination antibiotic treatment, that includes vancomycin and could be displaying symptoms that are potentially-indicative of DRESS. In this regard, a sample from the subject could be tested and the subject could be diagnosed as having vancomycin-induced DRESS when the presence of HLA-A*32:01 in the sample is detected. With such a diagnosis, antibiotic treatment could be adapted to exclude vancomycin.

Detecting and determining whether HLA-A*32:01 is present in the sample can be conducted using various techniques. For example, in some embodiments, sequence-based typing can be used. In some embodiments, SNP2HLA is used to determine whether HLA-A*32:01 is present in the sample.

In other embodiments, a polymerase chain reaction assay is used to determine whether HLA-A*32:01 is present in the sample. For example, in some embodiments, allele-specific polymerase chain reaction (AS-PCR) can be used, or quantitative polymerase chain reaction (qPCR) can be used.

The detection method can involve use of a primer mix including a primer specific for HLA-A*32 allele. For example, one or both of HLA-A*32 is HLA 32-88F (GACGACACGCAGTTCGTGCGGTT+T, LNA (SEQ ID NO: 1) and HLA032R2 (GAGCGCGATCCGCAGGC, STD (SEQ ID NO: 2)) can be used.

The primer mix can also include a primer targeting a housekeeping gene. For example, the housekeeping gene could be galactosylceramidase (GALC), and the primer specific for GALC could include one or both of GALc-F: TTACCCAGAGCCCTATCGTTCT (SEQ ID NO: 3) and GALC that is GALc-R: GTCTGCCCATCACCACCTATT (SEQ ID NO: 4).

In some embodiments of the method, in addition to determining whether HLA-A*32:01 is present in the sample, an IFN-γ Enzyme-Linked ImmuneSpot assay can be conducted.

The presently-disclosed subject matter includes kits containing reagents and/or tools useful for detecting whether HLA-A*32:01 is present in the sample. In some embodiments, the kit includes a primer specific for HLA-A*32. For example, the kit can include HLA 32-88F (GACGACACGCAGTTCGTGCGGTT+T, LNA (SEQ ID NO: 1)) and/or HLA-A*32 that is HLA032R2 (GAGCGC-GATCCGCAGGC, STD (SEQ ID NO: 2)). In some embodiments, the kit can also include a primer specific for a housekeeping gene. For example, the kit can include GALc-F: TTACCCAGAGCCCTATCGTTCT (SEQ ID NO: 3) and/or GALc-R: GTCTGCCCATCACCACCTATT (SEQ ID NO: 4).

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

Example 1

Vancomycin DRESS Cases

Retrospective patients were detected using Vanderbilt's BioVU repository, a deidentified electronic health record (EHR) database linked to a DNA biobank in operation since Feb. 7, 2007. Prospective patients with potential DRESS were enrolled to confirm genetic findings from the BioVU analysis using vancomycin-specific immunological studies to support clinical diagnoses. All patients prospectively enrolled from participating centers provided written or electronic consent. Institutional review board (IRB) approvals were in place for the BioVU study and for all sites contributing to the prospective study (Vanderbilt University Medical Center in Nashville (Tennessee, USA), Austin Health, Peter MacCallum Cancer Centre, and Alfred Health in Melbourne (Victoria, Australia), Fiona Stanley Hospital and Royal Perth Hospital in Perth (Western Australia, Australia)). Saliva and blood were routinely collected from prospective patients, processed and stored as repositories of DNA, peripheral blood mononuclear cells (PBMCs) and plasma. Patients >17 years of age who were diagnosed with DRESS with vancomycin identified as a primary implicated drug, a corresponding Naranjo adverse drug reaction score of ≥5 (probable adverse drug reaction), a RegiSCAR score of ≥4 (probable DRESS) and available DNA or genotyping were included in the study[5,6].

Vancomycin Tolerant Controls

Controls from the BioVU genotyped cohort (n=54,249) were defined as individuals who tolerated intravenous vancomycin for greater than 5 weeks and had at least five vancomycin therapeutic trough levels over the treatment period recorded in the Vanderbilt EHR. 297/54,249 individuals were prescribed at least 5 weeks of vancomycin treatment. Using this subset, controls were matched 2:1 with cases on sex, race and age within five years. Vancomycin tolerance and length of treatment was verified by manual review of the EHR by a reviewer blinded to the HLA results. Additional controls for vancomycin ELISpot assays were recruited from the Vanderbilt IRB-approved studies to investigate drug responses in individuals with a broad range of immune-mediated adverse drug reactions and healthy volunteers.

Human Leukocyte Antigen (HLA) Typing

High resolution four digit HLA A B C DP DR DQ typing was performed using either sequence-based typing on 454FLX or Illumina Miseq[7,8] or imputed from SNP data from HumanExome BeadChip and GWAS platforms by Expanded Multi-Ethnic Genotyping Array (MEGA$^{EX}$, Illumina), HumanOmni-Quad, HumanOmni5-Quad and Human660W-Quad using SNP2HLA as previously described[9]. Imputation for HLA-A*32:01 using SNP2HLA has a reported accuracy of 99.46%[9]. Associations between DRESS and carriage of HLA-A/B/C/DRB1/DQA1/DQB1/DPB1 alleles at the 4-digit level were assessed by conditional logistic regression to accommodate the matching. Analyses were carried out in R version 3.4.3. (R Core Team (2017)). R: A language and environment for statistical computing. R Foundation for Statistical Computing, Vienna, Austria. R-project.org/).

Enzyme-Linked ImmunoSpot (ELISpot) Assays

Overnight IFN-γ ELISpot assays were performed in triplicate (Mabtech Kit 3420-2H) as previously described[10-12] using negative (unstimulated) and positive (anti-CD3 Mabtech antibody and/or SEB) controls. PBMCs plated at 200,000 cells per well were incubated with pharmacy stock vancomycin and other implicated drugs at concentrations representative of peak serum concentrations (Cmax) as well as 10-fold higher and 10-fold lower than Cmax. A positive response was defined as >50 spot forming units (SFU)/million cells after background removal[10-12].

Time-to-Event Analysis of Vancomycin-Exposed BioVU Cohort

In the BioVU cohort of 54,249 patients with available genotyping, 137 patients were identified as HLA-A*32:01 positive and 1,672 who did not carry HLA-A*32:01 and for whom at least two weeks of intravenous vancomycin treatment was intended. 137 of the 1,672 HLA-A*32:01 negative individuals were randomly selected to serve as an equal-sized control group. The deidentified EHRs of the 274 patients in both sub-cohorts were reviewed during the period of vancomycin exposure to determine patient sex, race, age, longest treatment period, development of an adverse drug reaction (ADR) and specifically, the development of possible DRESS. Since DRESS is an immune-mediated reaction and vancomycin is renally cleared, patient immunosuppression, chronic renal failure and end stage renal failure with dialysis were documented as potential covariates. ADR latency, defined as the length of time from initiation of vancomycin to symptom onset, as well as any concurrent antimicrobials were documented. Analyses were carried out by Fisher's exact tests, logistic and Cox regression as appropriate in R version 3.4.3.

Skin Testing and Histopathology

Intradermal skin testing (IDT) with 0.05, 0.5, 5 and 50 mg/mL of sterile pharmacy grade vancomycin was performed with readings at 20 minutes, 24 and 48 hours on two patients: patient 18, a prospectively enrolled patient who had experienced probable vancomycin DRESS 6.5 months earlier and C51, an HLA-A*32:01 positive, vancomycin-naïve healthy control. For patient 18, histopathology was examined from the acute DRESS reaction and from a biopsy of the positive 5 mg/ml vancomycin delayed IDT. Formalin-fixed, paraffin-embedded skin biopsies were sectioned at 5 μm intervals. Slides were deparaffinized and stained with hematoxylin and eosin (H&E). For the immunohistochemistry (IHC), slides were placed on the Leica Bond Max IHC stainer and deparaffinized. Slides were incubated with anti-FOXP3 (Cat. 14-4777-82, eBioscience, Inc.) for one hour at a 1:100 dilution, Ready-To-Use anti-CD4 (PA0427, Leica) for one hour, or Ready-To-Use anti-CD8 (MM39-10, Stat-Lab) for 15 mins. The Bond Polymer Refine detection system was used for visualization. A dermatopathologist scored all slides.

Molecular Docking of Vancomycin with HLA-A*32:01

Sequences of HLA-A*32:01 and HLA-A*29:02 were obtained from the HLA/IGMT database (http://www.ebi.ac.uk/ipd/imgt/hla/allele.html). An atomic homology model for HLA-A*32:01 was generated with SWISS-MODELLER[13] based on the most closely related crystal structure, PDB 6EI2, 92% identical. To generate a peptide/HLA-A*32:01 complex model, the peptide from the crystal structure of 6EI2 was positioned into the antigen binding cleft of the HLA-A*32:01 model using SSM in the COOT program package, then mutated to RLYGKSLYSF, a peptide eluted from HLA-A*32:01[14]. The peptide/HLA-A*32:01 complex model was then geometry minimized using PHENIX[15].

Vancomycin was docked into the HLA-A*32:01 model with AutoDock Vina[16]. The scoring grid dimensions were 40×40×40 Å, centered on a site corresponding to the Cα of the fifth peptide amino acid (P5). Vancomycin was docked with exhaustiveness set to 40. The top nine scoring orientations were output and compared. PyMol was used to generate molecular graphics (The PyMOL Molecular Graphics System, Version 1.8 Schrödinger, LLC.).

Results

Baseline Demographics

Twenty-three individuals were identified that met inclusion criteria for clinically diagnosed vancomycin-associated DRESS in the study including 15 prospectively recruited patients (7 from Vanderbilt University Medical Center in Nashville, 5 from Melbourne, and 3 from Perth) and 8 retrospectively ascertained individuals from Vanderbilt's BioVU repository (Tables 1A and 1B). The patient cohort was primarily of European ancestry and included 9 women and 14 men from 17 to 76 years of age who developed DRESS between 2004 and 2018. All patients had Naranjo adverse drug reaction scores of 8 to 10 (probable or definite adverse drug reaction) and RegiSCAR scores of 4 to 7 (probable or definite DRESS). 21/23 (91%) patients were being treated with other antibiotics concurrently with vancomycin. The median latency period from vancomycin initiation to the first symptoms of DRESS was 21 days (mean, 22.9 days; range, 14-50 days) (Table 1A). Age, race and sex matching was successful (Table 6) and indications for vancomycin treatment were similar between cases and controls (Tables 1A and 6). Similar to the DRESS cases who had a median vancomycin trough of 16 g/mL (mean, 17.2 μg/mL; range, 3-44 μg/mL; n=116), the tolerant controls had a median vancomycin trough of 18 μg/mL (mean, 19.6 μg/mL; range, 2-86 μg/mL; n=644).

TABLE 1A

Summary of case basic demographics, clinical characteristics, HLA risk allele carriage and DRESS history.

| ID | Age | Sex | Race | Latency (Days) | Regi-SCAR | Naranjo | HLA-A*32:01 carriage | Trough (μg/mL) | Indication for vancomycin | Other implicated medications |
|---|---|---|---|---|---|---|---|---|---|---|
| 1 | 56 | F | W | 18 | 5 | 8 | Positive | 27 | MRSA cervical spine post-operative wound infection | rifampin |
| 2 | 52 | M | W | 26 | 6 | 8 | Positive | 9 | Culture negative post-operative soft tissue infection of right foot | ceftriaxone, ciprofloxacin |
| 3 | 59 | M | W | 19 | 4 | 8 | Positive | 14 | Gram-positive cocci right chronic calcaneal osteomyelitis | ciprofloxacin |
| 4 | 66 | M | W | 21 | 4 | 8 | Positive | 3 | MRSA osteomyelitis | rifampin |
| 5 | 27 | M | W/H | 29 | 5 | 8 | Positive | 21 | Lumbar spine osteomyelitis | isoniazid, rifampin, ethambutol, pyrazinamide |
| 6 | 33 | M | W | 28 | 5 | 8 | Positive | 14 | MRSE-infected mesh post bariatric surgery abdominal repair | None |
| 7 | 52 | M | W | 17 | 6 | 8 | Positive | 16 | Epidural abscess and osteomyelitis with Gram-positive bacteremia | ceftriaxone |
| 8 | 48 | M | B | 21 | 5 | 8 | Negative | 12 | Cellulitis post exploratory laparotomy and inguinal hernia repair | piperacillin-tazobactam |

TABLE 1A-continued

Summary of case basic demographics, clinical characteristics, HLA risk allele carriage and DRESS history.

| ID | Age | Sex | Race | Latency (Days) | Regi-SCAR | Naranjo | HLA-A*32:01 carriage | Trough (µg/mL) | Indication for vancomycin | Other implicated medications |
|---|---|---|---|---|---|---|---|---|---|---|
| 9 | 53 | F | W | 23 | 7 | 8 | Positive | 7 | Culture negative soft tissue infection with underlying rib osteomyelitis | levofloxacin, fluconazole |
| 10 | 29 | M | W | 26 | 5 | 8 | Positive | 19 | Traumatic arm injury and possible osteomyelitis | trimethoprim/ sulfa, methoxazole, piperacillin-tazobactam, ciprofloxacin |
| 11 | 58 | M | W | 36 | 6 | 8 | Positive | 22 | Culture negative osteomyelitis | ciprofloxacin |
| 12 | 62 | M | W | 21 | 4 | 8 | Negative | 21 | Implantable cardioverter defibrillator pocket infection | None |
| 13 | 17 | M | W | 29 | 4 | 8 | Positive | 10 | MRSA bacteremia secondary to right pelvic myositis and phlebitis | ibuprofen, hydroxyzine |
| 14 | 51 | F | W | 14 | 6 | 8 | Positive | 23 | *Enterococcus faecium* bacteremia | ceftazidime |
| 15 | 57 | M | W | 15 | 5 | 8 | Negative | 24 | Culture negative febrile neutropenia and neutropenic colitis during AML treatment | meropenem |
| 16 | 24 | F | W | 14 | 6 | 10 | Positive | 16 | MRSE and *Bacteroides fragilis* post-operative wound infection following caesarean section and supracervical hysterectomy for uterine necrosis | azithromycin, clindamycin, gentamicin, piperacillin-tazobactam, amoxicillin, meropenem, metronidazole |
| 17 | 38 | M | W | 18 | 5 | 8 | Positive | 14 | MRSA right chest phlegmon, deep soft tissue infection, underlying osteomyelitis of 2nd rib with fracture | rifampin |
| 18 | 47 | F | W | 17 | 6 | 8 | Positive | 13 | MRSA and *E. coli* bacteremia w/ chest infiltrate | levofloxacin |
| 19 | 76 | M | W | 27 | 6 | 8 | Positive | 12 | *Enterococcus* bacteremia and endocarditis | gentamicin, benzylpenicillin |
| 20 | 61 | F | W | 50 | 5 | 8 | Positive | N/A | MRSA wound infection leading to hip prosthesis removal and placement of vancomycin spacer | ciprofloxacin |
| 21 | 71 | F | W | 28 | 5 | 8 | Negative | 16 | MRSA and *E. coli* hardware infection post knee replacement | ceftriaxone, rifampin |
| 22 | 40 | F | W | 15 | 4 | 8 | Positive | 17 | *E. coli* and *Enterococcus faecalis* urosepsis during pregnancy | ceftriaxone |
| 23 | 47 | F | W | 15 | 5 | 8 | Positive | 22 | *Staphylococcus epidermis* ventriculitis | ceftriaxone |

Legend:
ID, patient identification;
Age, age at time of vancomycin treatment;
HLA, human leukocyte antigen;
Trough, last vancomycin trough level before development of hypersensitivity symptoms.
F, female;
M, male;
W, Caucasian;
W/H, Caucaisan/Hispanic;
B, African American;
N/A, not available;
MRSA, Methicillin-resistant *Staphylococcus aureus*;
MRSE, Methicillin-resistant *Staphylococcus epidermidis*;
AML, acute myeloid eukemia;
*E. coli, Escherichia coli.*

TABLE 1B

Additional hypersensitivity syndrome characteristics for vancomycin DRESS cases.
The length of the steroid tapers ranged from 4 weeks to >6 months. Data in quotes were taken directly from the electronic health records when laboratory values or medication records were not available. Where relevant creatinine values have been converted from umol/L to mg/dL.

| ID | Absolute Eosinophil Count (Cells/µL) | Resolution >15 days (Y/N) | Biopsy Supporting DRESS (Y/N) | Prior Exposure to Vancomycin >7 Days (Y/N) | Steroid Treatment Course |
|---|---|---|---|---|---|
| 1 | 17.4% (no absolute) | Y | Y | N | "1 dose of high dose steroids" |
| 2 | 2450 | Y | Y | N | Slow taper starting at 60 mg/day of prednisone |

TABLE 1B-continued

Additional hypersensitivity syndrome characteristics for vancomycin DRESS cases.
The length of the steroid tapers ranged from 4 weeks to >6 months. Data in quotes were taken
directly from the electronic health records when laboratory values or medication records were
not available. Where relevant creatinine values have been converted from umol/L to mg/dL.

| ID | Absolute Eosinophil Count (Cells/μL) | Resolution >15 days (Y/N) | Biopsy Supporting DRESS (Y/N) | Prior Exposure to Vancomycin >7 Days (Y/N) | Steroid Treatment Course |
|---|---|---|---|---|---|
| 3 | 680 | Y | Y | N | Slow taper starting at 80 mg/day of prednisone |
| 4 | 990 | Y | Y | N | None |
| 5 | 5480 | Y | Y | N | Slow taper starting at 60 mg/day of prednisone |
| 6 | 3610 | Y | Y | N | 1 mg/kg methylprednisolone, then slow taper starting at 80 mg/day of prednisone |
| 7 | 2770 | Y | Y | N | Slow taper starting at 40 mg/day of prednisone |
| 8 | 2400 | Y | N | N | None |
| 9 | 5290 | Y | Y | N | Slow taper starting at 60 mg/day of prednisone; 60 mg/day restarted 11 months after reaction for DRESS colitis |
| 10 | 2280 | Y | Y | U | None |
| 11 | 5100 | Y | Y | N | Slow taper starting at 60 mg/day of prednisone |
| 12 | 1840 | N | N | N | None |
| 13 | 1030 | Y | Y | N | Slow taper starting at 40 mg/day of prednisone |
| 14 | 1950 | Y | Y | N | 250 mg methylprednisolone, then slow taper starting at 5- mg/day of prednisone |
| 15 | 2150 | Y | Y | N | None |
| 16 | 3810 | Y | Y | N | Slow taper starting at 60 mg/day of prednisone |
| 17 | 710 | Y | Y | N | Slow taper starting at 30 mg/day of prednisone |
| 18 | 1470 | Y | Y | N | Slow taper starting at 80 mg/day of prednisone |
| 19 | 3180 | Y | N | U | "High dose steroids" |
| 20 | 6550 | Y | N | N | Slow taper starting at 80 mg/day of prednisone |
| 21 | 1230 | Y | Y | N | Slow taper starting at 12 mg/day or dexamethasone |
| 22 | 1200 | N | Y | N | None |
| 23 | 6000 | Y | Y | N | 100 mg/day hydrocortisone, then slow taper starting at 75 mg/day of prednisolone |

Legend: Y, yes; N, No; BSA, body surface area; U, Unknown.

TABLE 2

Results of the 1:2 case to control match.
Controls were identified using Vanderbilt's BioVU,
a deidentified electronic medical record database
linked to a DNA biobank.
Patients were matched on sex, race and age within five years.

| Case ID | Case Age | Case Sex | Case Race | Control ID | Control Age | Control Sex | Control Race |
|---|---|---|---|---|---|---|---|
| 1 | 56 | F | W | C1 | 57 | F | W |
|  |  |  |  | C2 | 56 | F | W |
| 2 | 52 | M | W | C3 | 53 | M | W |
|  |  |  |  | C4 | 51 | M | W |
| 3 | 59 | M | W | C5 | 57 | M | W |
|  |  |  |  | C6 | 60 | M | W |
| 4 | 66 | M | W | C7 | 66 | M | W |
|  |  |  |  | C8 | 65 | M | W |
| 5 | 27 | M | W/H | C9 | 22 | M | W |
|  |  |  |  | C10 | 28 | M | W |
| 6 | 33 | M | W | C11 | 33 | M | W |
|  |  |  |  | C12 | 37 | M | W |
| 7 | 52 | M | W | C13 | 50 | M | W |
|  |  |  |  | C14 | 50 | M | W |
| 8 | 48 | M | B | C15 | 52 | M | B |
|  |  |  |  | C16 | 43 | M | B |
| 9 | 53 | F | W | C17 | 54 | F | W |
|  |  |  |  | C18 | 57 | F | W |
| 10 | 29 | M | W | C19 | 32 | M | W |
|  |  |  |  | C20 | 26 | M | W |
| 11 | 58 | M | W | C21 | 59 | M | W |
|  |  |  |  | C22 | 56 | M | W |
| 12 | 62 | M | W | C23 | 62 | M | W |
|  |  |  |  | C24 | 62 | M | W |
| 13 | 17 | M | W | C25 | 18 | M | W |
|  |  |  |  | C26 | 17 | M | W |
| 14 | 51 | F | W | C27 | 51 | F | W |
|  |  |  |  | C28 | 51 | F | W |

TABLE 2-continued

Results of the 1:2 case to control match.
Controls were identified using Vanderbilt's BioVU,
a deidentified electronic medical record database
linked to a DNA biobank.
Patients were matched on sex, race and age within five years.

| Case ID | Case Age | Case Sex | Case Race | Control ID | Control Age | Control Sex | Control Race |
|---|---|---|---|---|---|---|---|
| 15 | 57 | M | W | C29 | 57 | M | W |
|  |  |  |  | C30 | 56 | M | W |
| 16 | 24 | F | W | C31 | 22 | F | W |
|  |  |  |  | C32 | 25 | F | W |
| 17 | 38 | M | W | C33 | 37 | M | W |
|  |  |  |  | C34 | 40 | M | W |
| 18 | 47 | F | W | C35 | 49 | F | W |
|  |  |  |  | C36 | 48 | F | W |
| 19 | 76 | M | W | C37 | 78 | M | W |
|  |  |  |  | C38 | 80 | M | W |
| 20 | 61 | F | W | C39 | 62 | F | W |
|  |  |  |  | C40 | 60 | F | W |
| 21 | 71 | F | W | C41 | 66 | F | W |
|  |  |  |  | C42 | 74 | F | W |
| 22 | 47 | F | W | C43 | 47 | F | W |
|  |  |  |  | C44 | 49 | F | W |
| 23 | 47 | F | W | C45 | 49 | F | W |
|  |  |  |  | C46 | 45 | F | W |

Legend:
ID, patient identification;
F, Female;
M, Male;
W, Caucasian;
W/H, Caucaisan/Hispanic;
B, African American.

TABLE 3

Demographics, HLA risk allele carriage and indication for vancomycin treatment for case-matched vancomycin tolerant individuals.

| ID | Age | Sex | Race | HLA-A*32:01 carriage | Indication for vancomycin treatment |
|---|---|---|---|---|---|
| C2 | 57 | F | W | Negative | Right orbital cellulitis with interconal and extraconal abscess |
| C2 | 56 | F | W | Negative | MRSA-infected failed aortobifemoral bypass graft |
| C3 | 53 | M | W | Negative | Tongue and pulmonary lesions concerning for infection in setting of AML |
| C4 | 51 | M | W | Negative | *Saccharomyces cerevisiae* pneumonia post bone marrow transplant |
| C5 | 57 | M | W | Negative | Scrotal abscess and probable rectus sheath hematoma infection |
| C6 | 60 | M | W | Negative | Osteomyelitis with abscess right heel |
| C7 | 66 | M | W | Negative | Osteomyelitis and sepsis secondary to diabetic foot infection |
| C8 | 65 | M | W | Negative | Mediastinal infection status post coronary artery bypass grafting |
| C9 | 22 | M | W | Negative | Pneumonia and neutropenic with persistent fevers in the setting of AML |
| C10 | 28 | M | W | Negative | Prosthetic aortic valve endocarditis with perivalvular abscess |
| C11 | 33 | M | W | Negative | Pneumonia and skin lesion in setting of neutropenia and CLL |
| C12 | 37 | M | W | Negative | Coagulase negative *Staphylococcus* native aortic valve endocarditis and septicemia |
| C13 | 50 | M | W | Negative | Native valve MSSA endocarditis with embolization to skin, brain and kidney and enterococcus in blood culture |
| C14 | 50 | M | W | Negative | Sepsis secondary to contaminated decubiti |
| C15 | 52 | M | B | Negative | Fever and altered mental status in the setting of HIV/AIDS |
| C16 | 43 | M | B | Negative | MRSA pneumonia in the setting of AIDS and end stage renal disease |
| C17 | 54 | F | W | Negative | MRSE infection of right total knee arthroplasty after liner exchange |
| C18 | 57 | F | W | Negative | MRSE-infected left chest port in setting of AML |
| C19 | 32 | M | W | Negative | Persistent fevers in the setting of Ewing's sarcoma on chemotherapy |
| C20 | 26 | M | W | Negative | Pneumonia in the setting of relapsed AML |
| C21 | 59 | M | W | Negative | MRSA bacteremia in the setting of chronic renal failure |
| C22 | 56 | M | W | Negative | Empiric vancomycin for cellulitis of foot with chronic non-healing wound following nail puncture |
| C23 | 62 | M | W | Negative | MRSE empyema in the setting of a single lung transplant |
| C24 | 62 | M | W | Negative | Donor-derived surgical culture growing *Staphylococcus aureus* after double lung transplant |
| C25 | 18 | M | W | Negative | Empiric therapy in patient with cystic fibrosis exacerbation and history of growing MSSA and *Pseudomonas* |
| C26 | 17 | M | W | Negative | Coagulase-negative staphylococcal bacteremia in the setting of hypoplastic left heart syndrome status post failed Fontan |
| C27 | 51 | F | W | Negative | Inferior ischiopubic ramus osteomyelitis |
| C28 | 51 | F | W | Negative | MRSA bacteremia and endocarditis of the atrioventricular valves with evidence of septic embolization |
| C29 | 57 | M | W | Negative | Coagulase-negative staphylococcal bacteremia status post autologous peripheral blood stem cell transplant |
| C30 | 56 | M | W | Negative | MRSA bacteremia in the setting of cellulitis of lower abdomen and possible endocarditis |
| C31 | 22 | F | W | Negative | Poly-Gram negative rod septicemia in the setting of orthotopic liver transplantation complicated |

TABLE 3-continued

Demographics, HLA risk allele carriage and indication for vancomycin treatment for case-matched vancomycin tolerant individuals.

| ID | Age | Sex | Race | HLA-A*32:01 carriage | Indication for vancomycin treatment |
|---|---|---|---|---|---|
| C32 | 25 | F | W | Negative | MRSA pneumonia in the setting of severe end stage cystic fibrosis |
| C33 | 37 | M | W | Negative | Left femur osteomyelitis and surrounding soft tissue infection at stump site of above knee amputation |
| C34 | 40 | M | W | Negative | Supracystic abscess communicating with the sigmoid colon after failed kidney/pancreas transplant status post explant of failed grafts |
| C35 | 49 | F | W | Negative | Probable pneumonia in the setting of splenic rupture and AML |
| C36 | 48 | F | W | Negative | Right toe osteomyelitis with overlying abscess positive for MRSA, *Enterococcus faecalis*, and *Providencia* status post amputation |
| C37 | 78 | M | W | Negative | MRSA-infected graft and right iliac region |
| C38 | 80 | M | W | Negative | Enterococcal septicemia |
| C39 | 62 | F | W | Negative | *Enterococcus faecalis* positive sacral decubitus ulcer with associated osteomyelitis |
| C40 | 60 | F | W | Negative | Fever and altered mental status in the setting of AML |
| C41 | 66 | F | W | Negative | Tibial osteomyelitis and hardware infection |
| C42 | 74 | F | W | Negative | MRSA-positive right shoulder prosthetic septic arthritis and sepsis |
| C43 | 47 | F | W | Negative | Necrotic anal mass with associated draining abscess |
| C44 | 49 | F | W | Negative | *Staphylococcal aureus* positive post-surgical meningitis and sepsis |
| C45 | 49 | F | W | Negative | Parapharyngeal abscess and cervical spine osteomyelitis with epidural abscess |
| C46 | 45 | F | W | Negative | MRSA osteomyelitis of the spine |

Legend:
ID, patient identification;
Age, age at time of vancomycin treatment;
HLA, human leukocyte antigen;
F, female;
M, male;
W, Caucasian;
B, African American;
MRSA, Methicillin-resistant *Staphylococcus aureus*;
AML, acute myeloid leukemia;
ALL, acute lymphoblastic leukemia;
CLL, chronic lymphoblastic leukemia;
MSSA, Methicillin-sensitive *Staphylococcus aureus*;
HIV/AIDS, human immunodeficiency virus/acquired immune deficiency syndrome;
MRSE, Methicillin-resistant *Staphylococcus epidermidis*.

HLA Associations with DRESS

The HLA-A*32:01 allele was carried by 19/23 (86%) DRESS cases compared with 0/46 (0%) of the matched vancomycin tolerant controls (p=1×10$^{-8}$, conditional logistic with Bonferroni multiple comparisons correction) (Tables 1, 6, 7 and 8 and FIG. 1A). In a larger BioVU cohort of DNA samples from 54,249 Vanderbilt patients, the HLA-A*32:01 allele carriage rate was 6.30% which is similar to that of other cohorts of predominant European ancestry[17]. Carriage of HLA-A*32:01 in the BioVU cohort was more prevalent in European Americans (6.78%) than African American populations (2.78%).

TABLE 4

Full HLA typing results of potential vancomycin DRESS cases.

| | HLA-A | | HLA-B | | HLA-C | | HLA-DPB1 | | HLA-DQA1 | | HLA-DQB1 | | HLA-DRB1 | |
|---|---|---|---|---|---|---|---|---|---|---|---|---|---|---|
| ID | Allele 1 | Allele 2 | Allele 1 | Allele 2 | Allele 1 | Allele 2 | Allele 1 | Allele 2 | Allele 1 | Allele 2 | Allele 1 | Allele 2 | Allele 1 | Allele 2 |
| 1 | 02:01 | 32:01 | 07:02 | 44:02 | 05:01 | 07:02 | 04:02 | 04:02 | NT | NT | 03:01 | 06:02 | 04:08 | 15:01 |
| 2 | 02:01 | 32:01 | 51:01 | 51:01 | 02:02 | 16:02 | 04:02 | 06:01 | 01:01 | 03:01 | 03:02 | 05:01 | 01:01 | 04:04 |
| 3 | | 32:01 | 40:01 | | 02:02 | 03:04 | | | | | | | | |
| 4 | 01:01 | 32:01 | 08:01 | 44:02 | 05:01 | 07:01 | 04:01 | 19:01 | NT | NT | 05:03 | 06:02 | 14 | 15 |
| 5 | 02:06 | 32:01 | 39:05 | 40:02 | 02:02 | 07:02 | 04:02 | 04:02 | 01:03 | 03:01 | 03:02 | 06:03 | 04:07 | 13:01 |
| 6 | 02:01 | 32:01 | 44:02 | 44:02 | 05:01 | 05:01 | 03:01 | 04:02 | 03:01 | 05:01 | 03:01 | 03:01 | 04:01 | 11:04 |
| 7 | 01:01 | 32:01 | 08:01 | 27:05 | 02:02 | 07:01 | 01:01 | 15:01 | 03:01 | 05:01 | 02:01 | 03:02 | 03:01 | 04:01 |
| 8 | 23:01 | 23:01 | 08:01 | 15:16 | 07:02 | 14:02 | 01:01 | 85:01 | 01:02 | 05:01 | 02:03 | 05:02 | 03:02 | 16:02 |
| 9 | 03:01 | 32:01 | 07:02 | 18:01 | 07:02 | 07:41 | 03:01 | 04:01 | NT | NT | 02:01 | 06:02 | 03:01 | 15:01 |
| 10 | 23:01 | 32:01 | 44:02 | 49:01 | 05:01 | 07:01 | 02:01 | 04:02 | 05:01 | 05:01 | 03:01 | 03:01 | 11:01 | 12:01 |
| 11 | 32:01 | 32:01 | 15:01 | 35:01 | 03:03 | 04:01 | 04:02 | 10:01 | 01:01 | 01:01 | 05:01 | 05:03 | 01:01 | 11:13 |
| 12 | 02:01 | 26:01 | 14:01 | 45:01 | 06:02 | 08:02 | 02:01 | 04:01 | 02:01 | 04:01 | 02:02 | 04:02 | 07:01 | 08:01 |
| 13 | 01:01 | 32:01 | 44:02 | 44:03 | 04:01 | 05:01 | 04:01 | 04:01 | 02:01 | 03:01 | 02:02 | 03:01 | 04:01 | 07:01 |
| 14 | 24:02 | 32:01 | 35:03 | 35:08 | 04:01 | 04:01 | 04:01 | 14:01 | 01:02 | 01:02 | 05:02 | 05:02 | 16:01 | 16:02 |
| 15 | 01:01 | 02:01 | 08:01 | 44:02 | 05:01 | 07:01 | 01:01 | 04:02 | 03:01 | 05:01 | 02:01 | 03:01 | 03:01 | 04:01 |
| 16 | 03:01 | 32:01 | 07:02 | 35:01 | 04:01 | 07:02 | 04:01 | 04:01 | 05:01 | 05:01 | 03:01 | 03:01 | 11:04 | 12:01 |
| 17 | 03:01 | 32:01 | 07:02 | 07:02 | 07:02 | 07:02 | 03:01 | 04:01 | 01:02 | 03:01 | 03:01 | 06:02 | 04:07 | 15:01 |
| 18 | 03:01 | 32:01 | 07:02 | 14:01 | 07:02 | 08:02 | 02:01 | 05:01 | 03:01 | 03:01 | 03:02 | 03:02 | 04:04 | 04:04 |

TABLE 4-continued

Full HLA typing results of potential vancomycin DRESS cases.

| | HLA-A | | HLA-B | | HLA-C | | HLA-DPB1 | | HLA-DQA1 | | HLA-DQB1 | | HLA-DRB1 | |
|---|---|---|---|---|---|---|---|---|---|---|---|---|---|---|
| ID | Allele 1 | Allele 2 | Allele 1 | Allele 2 | Allele 1 | Allele 2 | Allele 1 | Allele 2 | Allele 1 | Allele 2 | Allele 1 | Allele 2 | Allele 1 | Allele 2 |
| 19 | 01:01 | 32:01 | 13:02 | 51:01 | 06:02 | 14:02 | 01:01 | 04:01 | 02:01 | 02:01 | 02:02 | 02:02 | 07:01 | 07:01 |
| 20 | 68:01 | 32:01 | 13:02 | 51:01 | 02:02 | 06:02 | 02:01 | 04:01 | 02:01 | 03:01 | 02:02 | 03:03 | 07:01 | 09:01 |
| 21 | 01:01 | 03:01 | 07:02 | 08:01 | 07:01 | 07:02 | 03:01 | 04:01 | 01:02 | 05:01 | 03:01 | 06:02 | 11:01 | 15:01 |
| 22 | 03:01 | 32:01 | 15:01 | 44:02 | 03:04 | 05:01 | 02:01 | 11:01 | 01:01 | 02:01 | 02:02 | 05:02 | 01:01 | 11:01 |
| 23 | 24:02 | 32:01 | 08:01 | 40:01 | 03:04 | 07:01 | 02:01 | 04:02 | 03:01 | 05:01 | 02:01 | 03:02 | 03:01 | 04:04 |

Empty wells could not be imputed.
Legend:
ID, patient identification;
HLA, human leukocyte antigen;
NT, not typed.

TABLE 5

Full HLA typing results of vancomycin tolerant controls.

| | HLA-A | | HLA-B | | HLA-C | | HLA-DPB1 | | HLA-DQA1 | | HLA-DQB1 | | HLA-DRB1 | |
|---|---|---|---|---|---|---|---|---|---|---|---|---|---|---|
| ID | Allele 1 | Allele 2 | Allele 1 | Allele 2 | Allele 1 | Allele 2 | Allele 1 | Allele 2 | Allele 1 | Allele 2 | Allele 1 | Allele 2 | Allele 1 | Allele 2 |
| C1 | 01:01 | 24:02 | 08:01 | 08:01 | 07:01 | 07:01 | 01:01 | 13:01 | 01:02 | 05:01 | 02:01 | 06:02 | 03:01 | 15:01 |
| C2 | 01:01 | 02:01 | 08:01 | 44:02 | 07:01 | 07:04 | 04:01 | 11:01 | 02:01 | 05:01 | 02:02 | 03:01 | 07:01 | 11:01 |
| C3 | 03:01 | 11:01 | 07:02 | 07:02 | 07:02 | 07:02 | 03:01 | 04:01 | 03:01 | 03:01 | 03:01 | 03:02 | 04:01 | 04:04 |
| C4 | 02:01 | 29:02 | 07:02 | 44:03 | 07:02 | 16:01 | 04:01 | 04:02 | 01:01 | 02:01 | 02:02 | 05:01 | 07:01 | 10:01 |
| C5 | 03:01 | 26:01 | 35:01 | 45:01 | 04:01 | 06:02 | 04:01 | 09:01 | 01:01 | 01:01 | 05:01 | 05:01 | 01:01 | 01:01 |
| C6 | 01:01 | 02:01 | 18:01 | 57:01 | 06:02 | 07:01 | 04:01 | 04:01 | 01:02 | 02:01 | 03:03 | 06:02 | 07:01 | 15:01 |
| C7 | 01:01 | 03:01 | 07:02 | 57:01 | 06:02 | 07:02 | 04:01 | 04:01 | 01:02 | 02:01 | 03:03 | 06:02 | 07:01 | 15:01 |
| C8 | 01:01 | 02:01 | 18:01 | 50:01 | 06:02 | 07:01 | 03:01 | 14:01 | 01:01 | 02:01 | 02:02 | 05:01 | 01:01 | 07:01 |
| C9 | 02:01 | 03:01 | 15:18 | 40:01 | 03:04 | 07:04 | 02:01 | 04:01 | 01:01 | 01:02 | 05:01 | 06:02 | 01:02 | 15:01 |
| C10 | 01:01 | 24:02 | 37:01 | 55:01 | 03:03 | 06:02 | 02:01 | 02:01 | 01:02 | 05:01 | 03:01 | 06:04 | 12:01 | 13:02 |
| C11 | 25:01 | 29:02 | 15:01 | 44:02 | 03:04 | 05:01 | 02:01 | 03:01 | 03:01 | 03:01 | 03:02 | 03:02 | 04:01 | 04:01 |
| C12 | 02:01 | 11:01 | 44:02 | 50:01 | 05:01 | 06:02 | 04:01 | 04:01 | 01:02 | 03:01 | 03:01 | 06:02 | 04:08 | 15:01 |
| C13 | 01:01 | 03:01 | 18:01 | 40:02 | 02:02 | 07:01 | 04:01 | 04:01 | 01:01 | 05:01 | 03:01 | 05:01 | 01:01 | 11:04 |
| C14 | 02:01 | 03:01 | 44:02 | 51:01 | 01:02 | 07:04 | 03:01 | 03:01 | 01:01 | 05:01 | 03:01 | 05:01 | 01:01 | 11:01 |
| C15 | 30:02 | 66:02 | 07:02 | 07:02 | 07:01 | 15:05 | 02:01 | 17:01 | 01:01 | 01:02 | 05:01 | 05:01 | 10:01 | 11:01 |
| C16 | 23:01 | 30:01 | 07:02 | 18:01 | 02:10 | 07:02 | 01:01 | 18:01 | 01:02 | 01:02 | 06:02 | 06:02 | 11:01 | 15:03 |
| C17 | 01:01 | 02:01 | 08:01 | 08:01 | 07:01 | 07:01 | 01:01 | 01:01 | 05:01 | 05:01 | 02:01 | 02:01 | 03:01 | 03:01 |
| C18 | 26:01 | 68:02 | 15:01 | 15:07 | 03:03 | 05:01 | 04:01 | 11:01 | 01:02 | 01:03 | 06:02 | 06:03 | 13:01 | 15:01 |
| C19 | 02:01 | 02:01 | 15:82 | 44:02 | 03:03 | 05:01 | 04:01 | 04:02 | 03:01 | 05:01 | 03:02 | 03:02 | 04:01 | 11:01 |
| C20 | 01:01 | 68:01 | 08:01 | 39:01 | 07:01 | 07:02 | 03:01 | 04:01 | 01:02 | 03:01 | 03:02 | 06:02 | 04:07 | 15:01 |
| C21 | 01:01 | 11:01 | 40:02 | 51:01 | 01:02 | 02:02 | 04:01 | 04:01 | 01:01 | 05:01 | 03:01 | 05:03 | 11:01 | 14:01 |
| C22 | 03:01 | 03:01 | 07:02 | 15:01 | 03:03 | 07:02 | 03:01 | 04:01 | 03:01 | 03:01 | 03:01 | 05:01 | 01:03 | 04:01 |
| C23 | 02:01 | 68:01 | 40:01 | 55:01 | 03:03 | 03:04 | 03:01 | 05:01 | 01:01 | 03:01 | 03:01 | 05:03 | 04:01 | 14:01 |
| C24 | 02:01 | 11:01 | 44:02 | 52:01 | 05:01 | 12:02 | 04:01 | 04:01 | 01:01 | 01:02 | 05:03 | 06:02 | 14:04 | 15:01 |
| C25 | 01:01 | 01:01 | 15:01 | 44:02 | 03:03 | 05:01 | 04:01 | 19:01 | 01:03 | 01:03 | 06:03 | 06:03 | 13:01 | 13:02 |
| C26 | 02:01 | 24:02 | 40:02 | 44:02 | 01:02 | 02:02 | 02:01 | 04:01 | 01:01 | 05:01 | 03:01 | 05:01 | 01:03 | 11:01 |
| C27 | 03:01 | 03:01 | 07:02 | 51:01 | 01:02 | 07:02 | 03:01 | 04:01 | 01:01 | 01:02 | 05:01 | 06:02 | 01:01 | 15:01 |
| C28 | 23:01 | 24:02 | 49:01 | NT | 03:03 | 07:01 | 01:01 | 04:01 | 02:01 | 05:01 | 02:02 | 03:01 | 07:01 | 11:01 |
| C29 | 25:01 | 29:02 | 18:01 | 44:02 | 05:01 | 12:03 | 03:01 | 04:01 | 01:02 | 03:01 | 03:01 | 06:02 | 04:01 | 15:01 |
| C30 | 02:01 | 02:01 | 15:01 | 44:02 | 03:04 | 05:01 | 04:01 | 20:01 | 01:01 | 03:01 | 03:02 | 05:03 | 04:01 | 14:01 |
| C31 | 02:01 | 02:01 | 15:01 | 44:02 | 03:04 | 05:01 | 03:01 | 04:01 | 01:02 | 01:03 | 06:02 | 06:03 | 13:01 | 15:01 |
| C32 | 03:01 | 11:01 | 35:01 | 56:01 | 04:01 | 04:01 | 04:01 | 04:02 | 01:02 | 01:02 | 06:02 | 06:02 | 15:01 | 15:01 |
| C33 | 02:01 | 02:01 | 27:02 | 44:02 | 02:02 | 05:01 | 04:02 | 04:02 | 03:01 | 03:01 | 03:02 | 03:02 | 04:01 | 04:04 |
| C34 | 01:01 | 23:01 | 08:01 | 49:01 | 07:01 | 07:01 | 01:01 | 01:01 | 03:01 | 05:01 | 02:01 | 03:02 | 03:01 | 04:05 |
| C35 | 01:01 | 01:01 | 14:01 | 57:01 | 06:02 | 06:02 | 05:01 | 13:01 | 02:01 | 02:01 | 02:02 | 03:03 | 07:01 | 07:01 |
| C36 | 01:01 | 02:01 | 08:01 | 57:01 | 06:02 | 07:01 | 03:01 | 04:01 | 02:01 | 05:01 | 02:01 | 03:03 | 03:01 | 07:01 |
| C37 | 02:01 | 29:02 | 44:03 | 44:03 | 16:01 | 16:01 | 01:01 | 03:01 | 02:01 | 02:01 | 02:02 | 02:02 | 07:01 | 07:01 |
| C38 | 02:01 | 11:01 | 08:01 | 55:01 | 03:03 | 07:01 | 02:01 | 04:01 | 03:01 | 05:01 | 02:01 | 03:01 | 03:01 | 04:07 |
| C39 | 03:01 | 25:01 | 07:02 | 18:01 | 07:02 | 12:03 | 04:01 | 04:01 | 01:02 | 01:02 | 06:02 | 06:02 | 15:01 | 15:01 |
| C40 | 01:01 | 02:01 | 08:01 | 08:01 | 07:01 | 07:01 | 01:01 | 03:01 | 05:01 | 05:01 | 02:01 | 02:01 | 03:01 | 03:01 |
| C41 | 02:01 | 02:02 | 15:01 | 44:02 | 03:03 | 05:01 | 02:01 | 04:01 | 03:01 | 05:01 | 03:01 | 03:01 | 04:01 | 12:01 |
| C42 | 02:01 | 03:01 | 07:02 | 07:02 | 07:02 | 07:02 | 01:01 | 04:01 | 05:01 | 05:01 | 02:01 | 02:01 | 03:01 | 03:01 |
| C43 | 03:01 | 30:01 | 07:02 | 40:02 | 02:02 | 07:02 | 04:01 | 04:01 | 01:02 | 05:01 | 03:01 | 06:02 | 11:01 | 15:01 |
| C44 | 01:01 | 26:01 | 08:01 | 38:01 | 07:01 | 12:03 | 01:01 | 04:01 | 01:02 | 05:01 | 02:01 | 06:04 | 03:01 | 13:02 |
| C45 | 01:01 | 31:01 | 08:01 | 40:01 | 03:04 | 07:01 | 03:01 | 04:01 | 01:02 | 05:01 | 02:01 | 06:02 | 03:01 | 15:01 |
| C46 | 29:02 | 31:01 | 07:02 | 49:01 | 07:01 | 07:02 | 03:01 | 03:01 | 01:02 | 03:01 | 03:02 | 06:02 | 04:05 | 15:01 |

Legend:
ID, patient identification;
HLA, human leukocyte antigen;
NT, not typed.

TABLE 5A

Demographics and HLA risk allele carriage for vancomycin ELISpot negative patients who developed non-DRESS adverse reactions to vancomycin.

| ID | Age | Sex | Race | Adverse Reaction | HLA-A*32:01 |
|---|---|---|---|---|---|
| C51 | 57 | F | W | Delayed rash | Negative |
| C52 | 51 | M | W | Linear AgA Bullous Dermatosis | Negative |
| C53 | 47 | M | W | Linear AgA Bullous Dermatosis | Negative |
| C54 | 28 | F | W | Fixed Drug Eruption | Negative |
| C55 | 64 | F | W | Acute Generalized Exanthematous Pustulosis | Positive |

Legend:
ID, patient identification;
AGE, age at tome of vancomycin treatment;
HLA, human leukocyte antigen;
F, female;
M, male;
W, Caucasian.

IFN-γ ELISpot Responses in DRESS

Figure 5A:
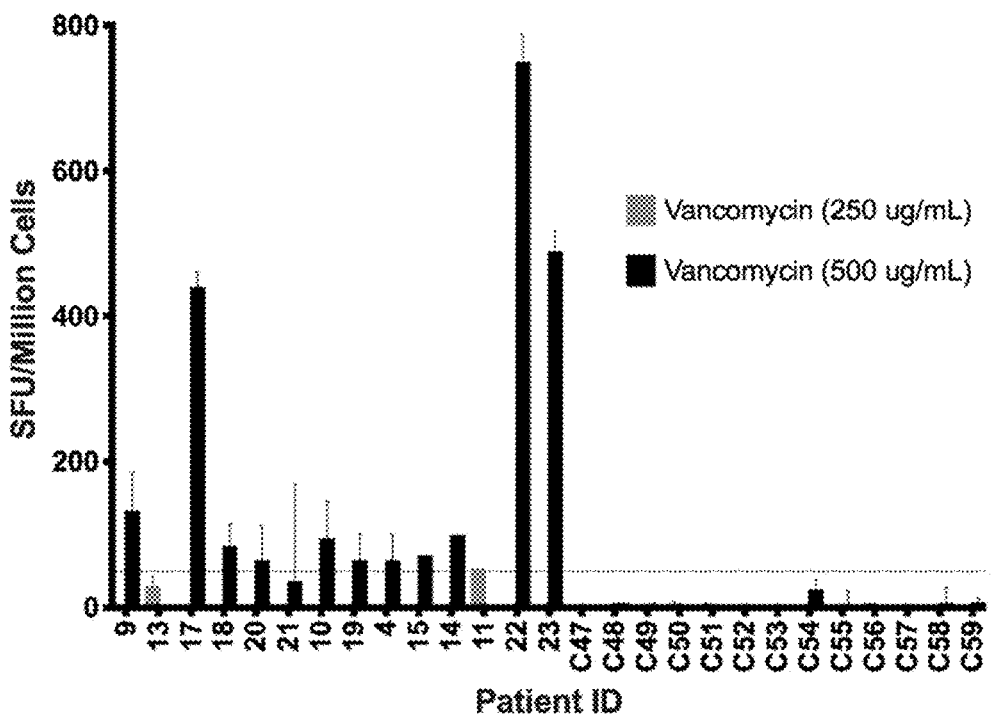
FIGS. 5A and 5B. Vancomycin IFN-γ release ELISpot results FIG. 5A. IFN-γ release ELISpot results after overnight stimulation with vancomycin at concentrations of 250 μg/mL (grey) or 500 μg/mL (black) using peripheral blood mononuclear cells (PBMCs) from vancomycin DRESS patients. Controls included cells from vancomycin-naïve, HLA-A*32:01 positive healthy donors (C47, C49-C50) including the son of case patient 18 (C49) and the vancomycin skin test negative control (C50), an HLA-A*32:01 positive individual tolerant of 4 weeks of vancomycin (C48), patients who had developed a non-DRESS immune-mediated adverse reaction to vancomycin (C51-C55) and non-HLA matched healthy donors (C56-C59). None of the controls released IFN-γ in response to vancomycin stimulation. Patient and control PBMCs were also stimulated with vancomycin at concentrations of 5 μg/mL and 50 μg/mL and exhibited a dose-dependent response (data not shown). In patients with multiple blood draws at time points distant from the reaction, ELISpot results from the first blood draw are plotted. Means of the replicates are plotted. Error bars indicate standard deviations of the mean after background subtraction. Positive results are those above the dotted line intersecting the y-axis at 50 SFU/million cells.
Figure 5B:
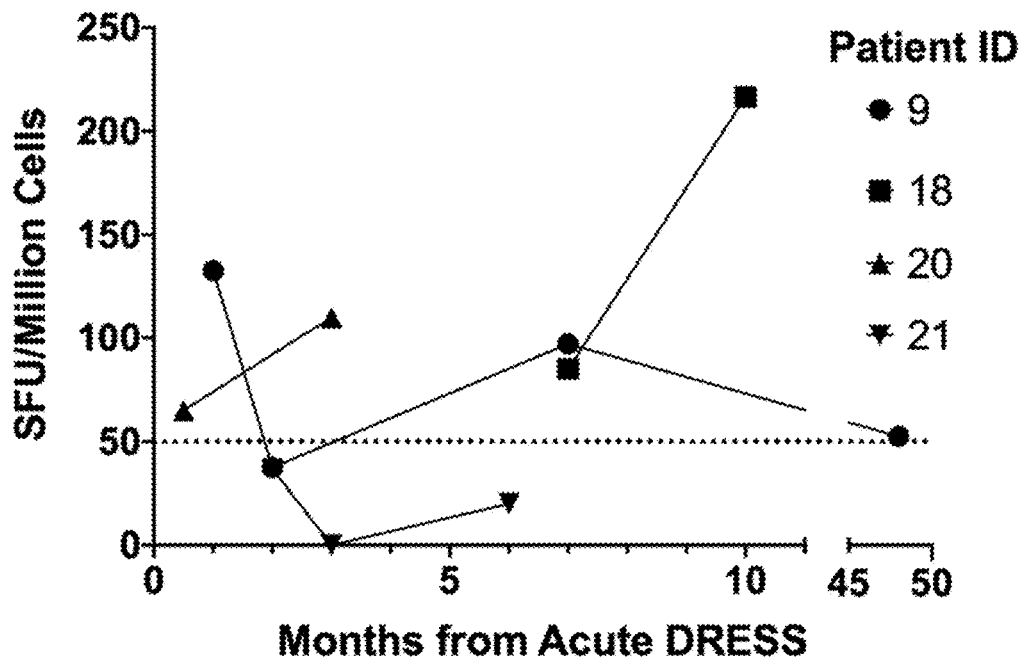
Figure 6:
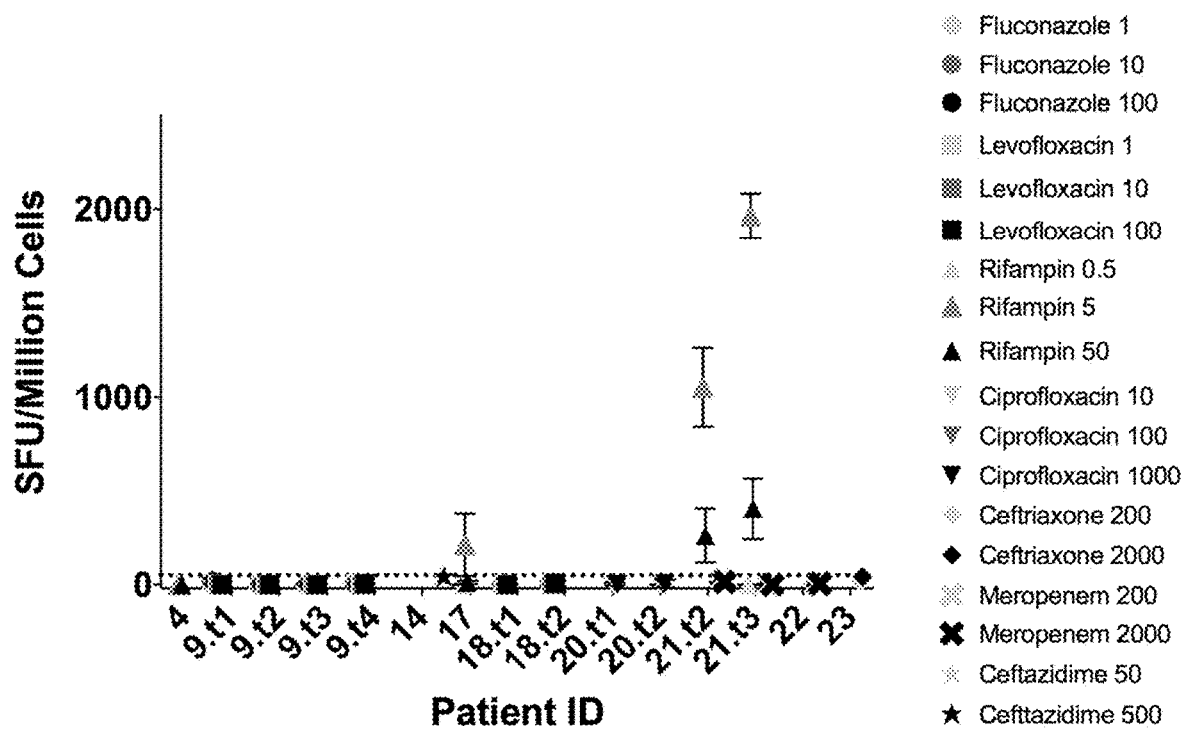
FIG. 6. IFN-γ release ELISpot results using peripheral blood mononuclear cells from DRESS patients after overnight stimulation with all medications taken concurrently with vancomycin. All drugs were tested at μg/mL concentrations. Counting from the start of DRESS symptoms, sample time points were at one month, two months, seven months and four years for patient 9, seven months and ten months for patient 18, twelve days and three months for patient 20, and three months and six months for patient 21. Cells from Patient 21 who did not respond to vancomycin stimulation and does not carry the HLA-A*32:01 risk allele had a strong response to rifampin stimulation. Cells from Patient 17 who does carry the risk allele and did respond to ex vivo vancomycin stimulation also had a positive response to rifampin. However, cells from Patient 4 and other healthy donors did not respond to rifampin stimulation. No other patient samples tested released IFN-γ in response to stimulation from any other medication. Means of the replicates are plotted. Error bars indicate standard deviations of the mean after background subtraction. Positive results are those above the dotted line intersecting the y-axis at 50 SFU/million cells. The figure was generated using GraphPad Prism 7.0a Macintosh Version, GraphPad Software, La Jolla California USA, graphpad.com. Legend: Patient ID, patient identification; SFU, spot-forming units.
Figures 7A, 7B:
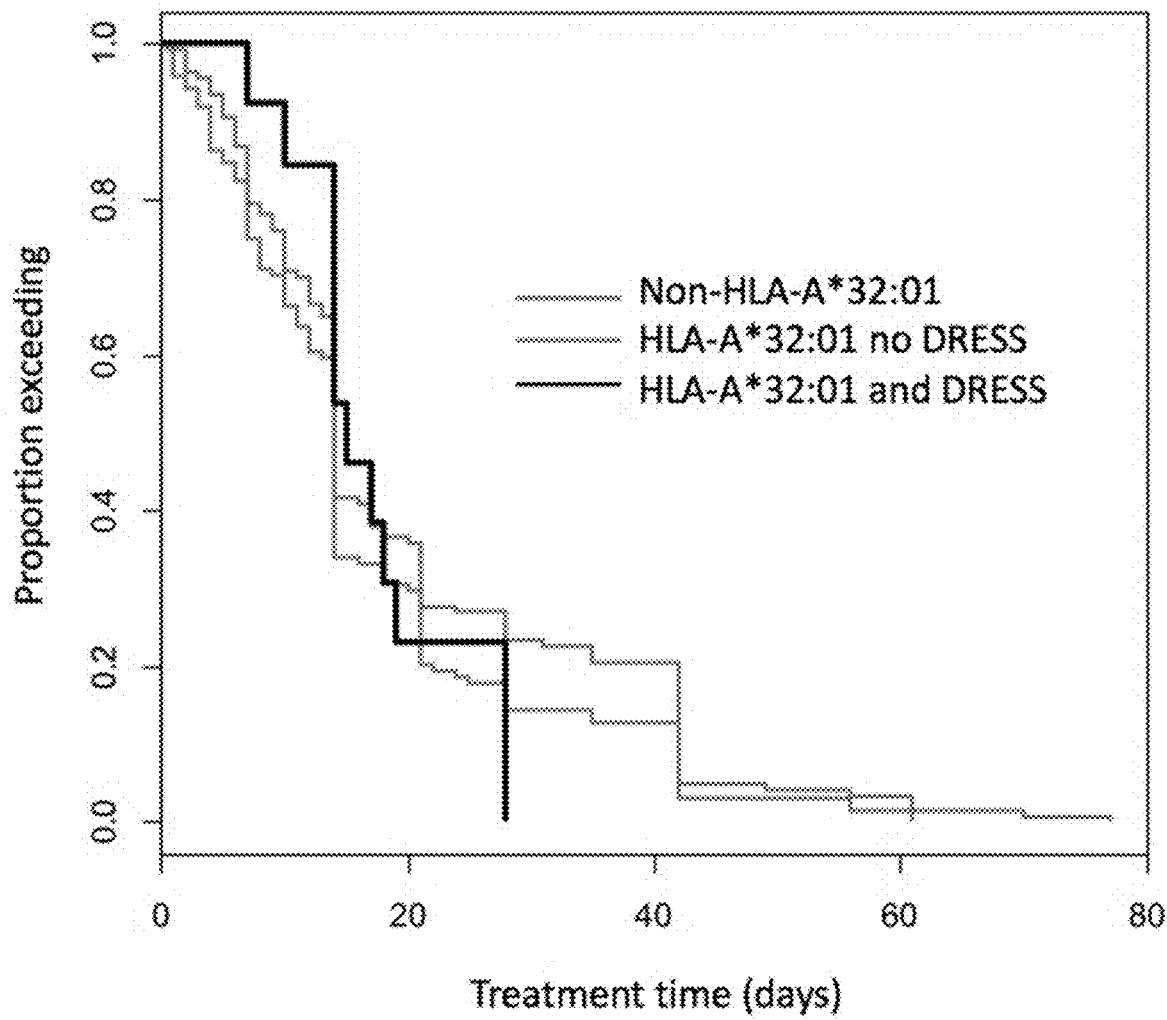
FIGS. 7A and 7B. Summary of vancomycin-exposed BioVU Cohort. None of the factors including age, longest treatment length, sex, race and overall adverse drug reaction rate differed significantly between the HLA-A*32:01 positive and HLA-A*32:01 negative groups (t-tests or Fisher exact tests as appropriate). In a joint logistic regression with vancomycin DRESS as response, none of the other factors including age, treatment length, sex and race were significant individually (p>0.4) or jointly (p=0.95) after adjusting for HLA-A*32:01, nor did they abrogate the significance of HLA-A*32:01 (p=0.00014, all based on likelihood ratio tests). 3/13 vancomycin DRESS cases overlapped with the previously identified BioVU cases (Patients 1, 6 and 7 from Table 1).
Figure 8:
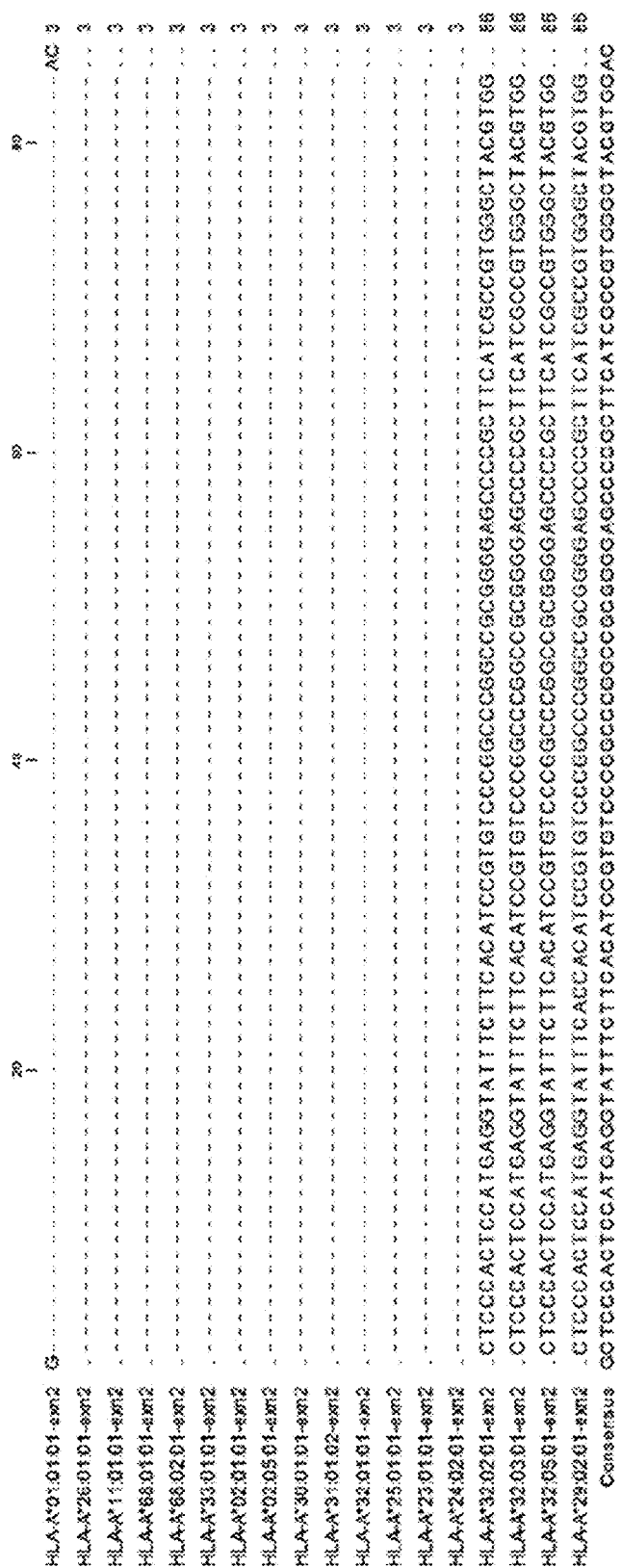
FIG. 8: Binding sites and properties of HLA-A*32:01 primers. Sequences from IMGT/HLA database were aligned with HLA-A*01:01:01 using CLC Genomics Workbench 9. Identical bases to the reference sequence (HLA-A*01:01:01) are represented as dots. The LNA Primer: HLA 32-88F: ACACGCAGTTCGTGCGGTT+T (SEQ ID NO: 1) is locked at the T position which is unique to HLA-A*32 alleles as well as HLA-A*29:02. The reverse primer: HLA032R2:GAGCGCGATCCGCAGGC (SEQ ID NO: 2) is also shown, but this one does not target HLA-A*29:02. This assay ensures amplification of HLA-A*32 allele only.
Figure 9A:
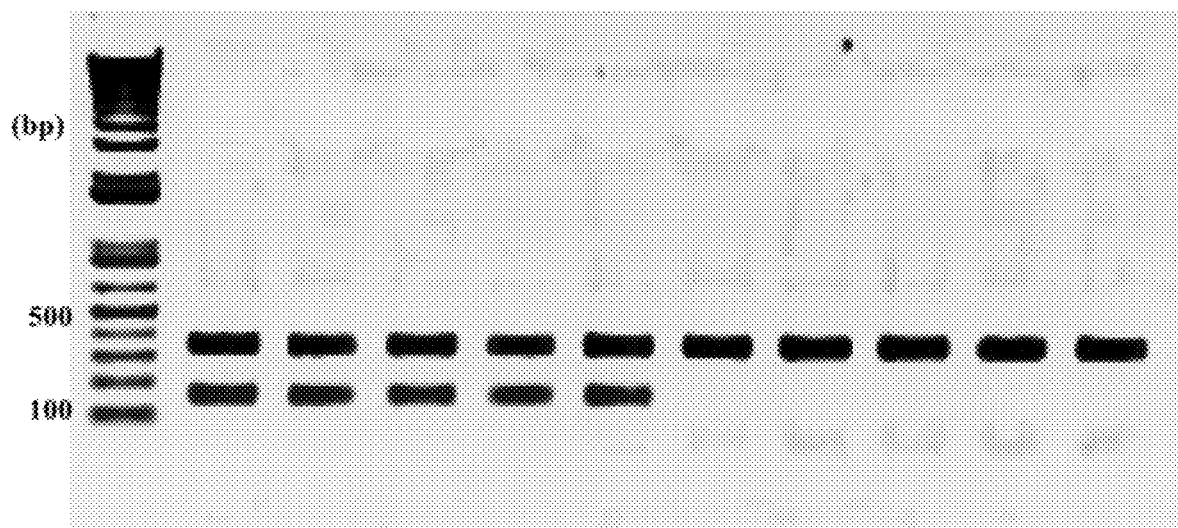
FIGS. 9A-9D: AS-PCR results.
Figure 9B:
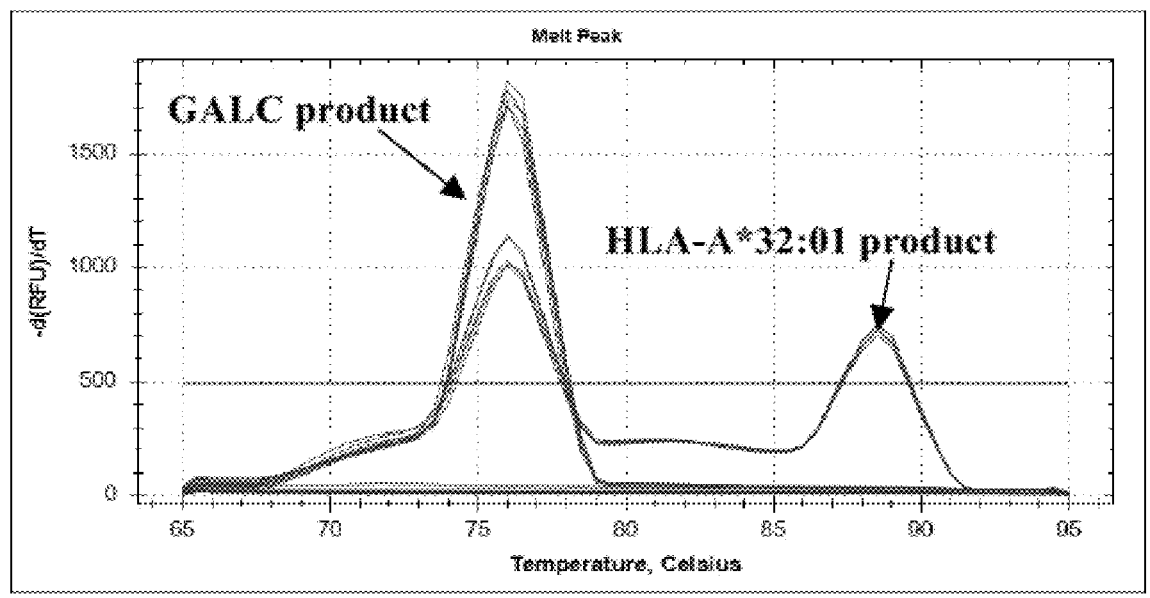
Figure 9C:
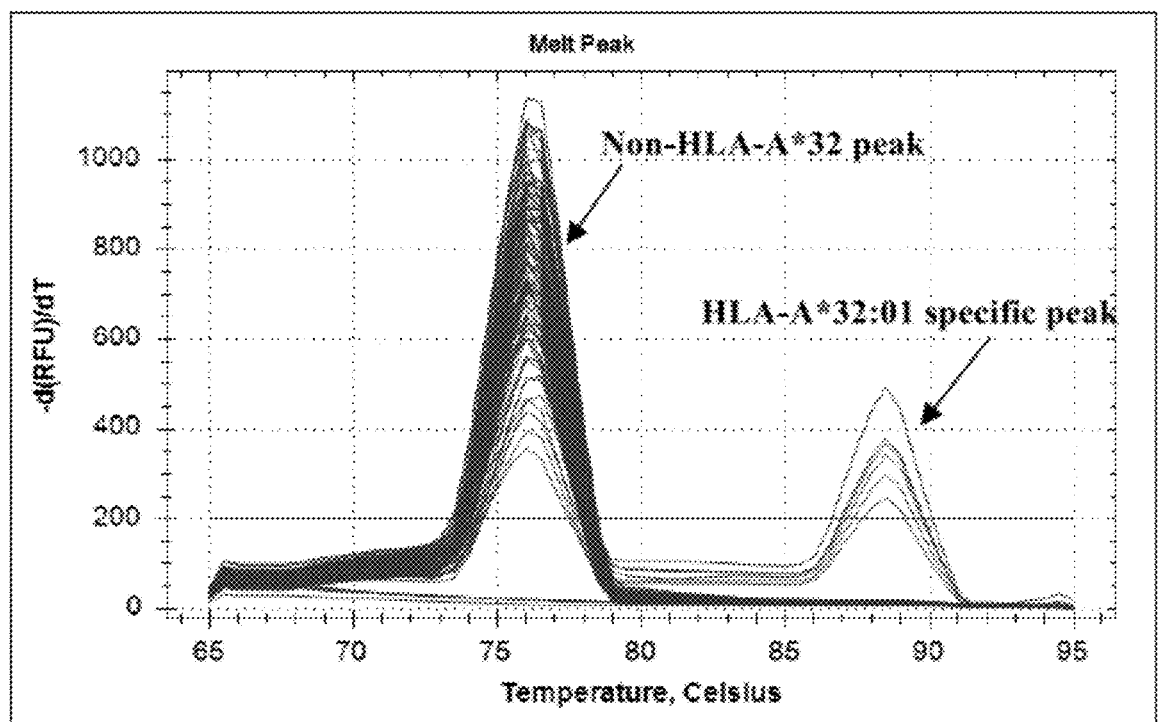
Figure 9D:
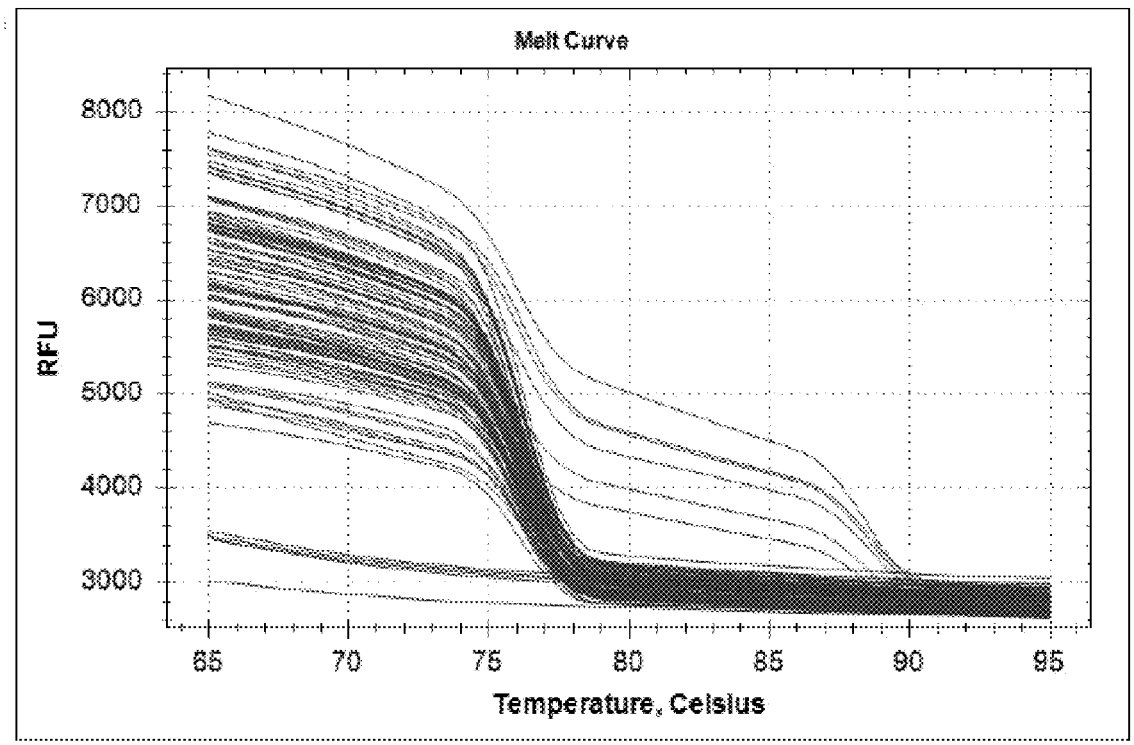

IFN-γ ELISpot assays were performed on all prospectively enrolled cases for which cryopreserved PBMCs were available (14/15). PBMCs from 12/14 (86%) DRESS cases had a positive IFN-γ ELISpot response to vancomycin (FIGS. 1B and 5A). Analyses restricted to immunologically confirmed cases and matched controls, revealed that 11/12 (92%) IFN-γ ELISpot positive patients carried HLA-A*32:01 compared with 0/24 (0%) of the matched controls (p=9× $10^{-7}$, conditional logistic) (FIG. 1A). Three IFN-γ ELISpot positive patients had multiple blood draws at time points distant from the initial reaction with repeat positive results (FIG. 5B). In Patient 4, a positive IFN-γ ELISpot to vancomycin was demonstrated 9 years after the initial DRESS reaction. In samples with sufficient cell numbers, PBMCs were routinely tested against all other concurrently administered medications potentially implicated in DRESS development (FIG. 6). Notably, patient 21, one of the two patients with a negative vancomycin IFN-γ ELISpot, is HLA-A*32:01 negative and demonstrated a reproducible positive IFN-γ ELISpot to rifampin stimulation leading us to conclude that her DRESS syndrome was associated with rifampin. Thirteen controls were tested concurrently with cases and none demonstrated a positive vancomycin IFN-γ ELISpot (FIGS. 1B and 5A).

Time to DRESS Analysis of the Vancomycin-Exposed BioVU Cohort

Figure 2:
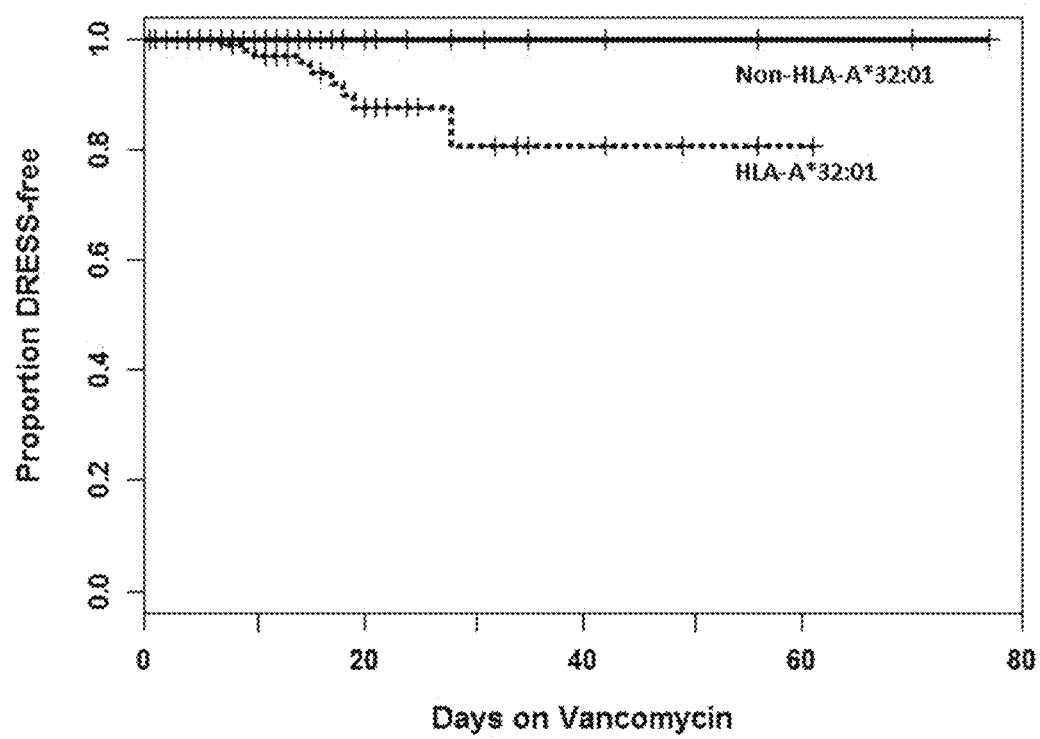
FIG. 2. Kaplan-Meier estimates of time to DRESS or possible DRESS development during vancomycin treatment stratified by carriage of HLA-A*32:01. Cases of DRESS occurred in HLA-A*32:01 positive subjects between 1 and 4 weeks after starting vancomycin but not in HLA-A*32:01 negative subjects. The estimated risk of DRESS prior to 4 weeks of treatment was 19.2% in those carrying the HLA-A*32:01 allele.
Figure 4:
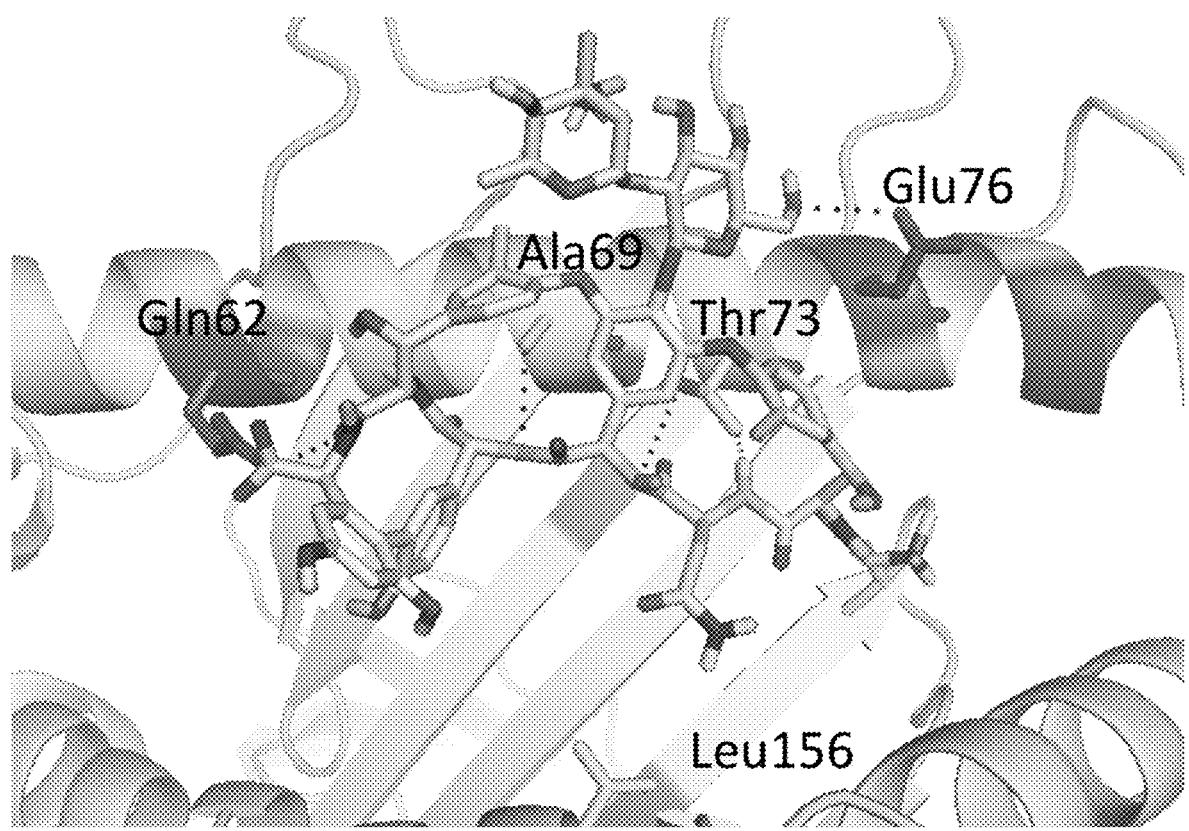
FIG. 4. Molecular docking prediction of vancomycin binding HLA-A*32:01. Vancomycin is shown as sticks, white for carbon, blue for nitrogen, red for oxygen. Vancomycin atoms that mediate intermolecular contacts with D-Ala-D-Ala (in PDB 1FVM) are shown in cyan. A homology model of HLA-A*32:01 is shown in yellow as a ribbon diagram. Polymorphic positions that distinguish the associated HLA-A*32:01 allele from the closely related HLA-A*29:02 allele are shown in magenta. Intermolecular contacts between vancomycin and HLA-A*32:01 predicted by molecular docking are shown as black dashes.

While at least two weeks of vancomycin was intended in all patients, 22/137 (16%) HLA-A*32:01 positive and 18/137 (13%) HLA-A*32:01 negative patients completed <1 week of vancomycin therapy. Possible and definitive DRESS cases in the HLA-A*32:01 carriers occurred one week to four weeks after starting vancomycin and the estimated probability of developing DRESS was 19.2% at four weeks (FIGS. 2 and 4). In comparison, none of the 119 HLA-A*32:01 negative individuals who were exposed to at least one week of uninterrupted vancomycin treatment developed DRESS or symptoms suggestive of DRESS (p=6×$10^{-5}$). The median time to DRESS symptoms after vancomycin initiation was 18 days in this cohort. Development of non-DRESS ADRs did not differ between risk allele positive and negative groups (p=0.35). Within the HLA-A*32:01 positive group, when considered jointly by logistic regression with DRESS as outcome, hemodialysis (p=0.03) and immunosuppression (p=0.04) were both protective factors against DRESS development. Among the DRESS cases, 2/13 (15%) had either hemodialysis or immunosuppression compared with 64/124 (52%) carrying HLA-A*32:01 who tolerated vancomycin (p=0.02). Notably, 18 HLA-A*32:01 positive individuals tolerated vancomycin for ≥5 weeks. This demonstrates that not all HLA-A*32:01 positive individuals will develop DRESS after prolonged vancomycin treatment.

Skin Testing, Oral Rechallenge, and Skin Histology Results

Figure 3A:
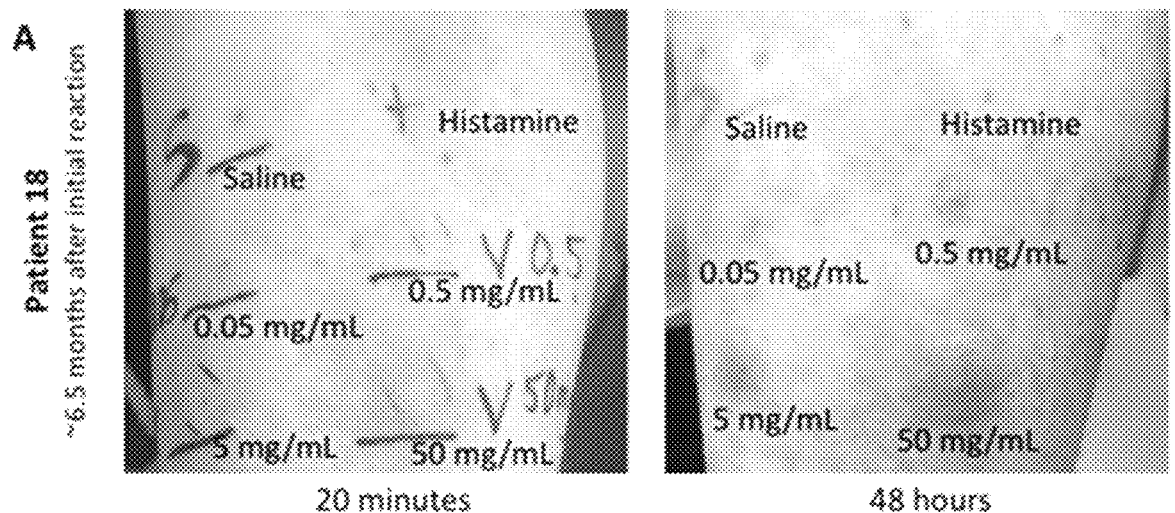
Figure 3E:
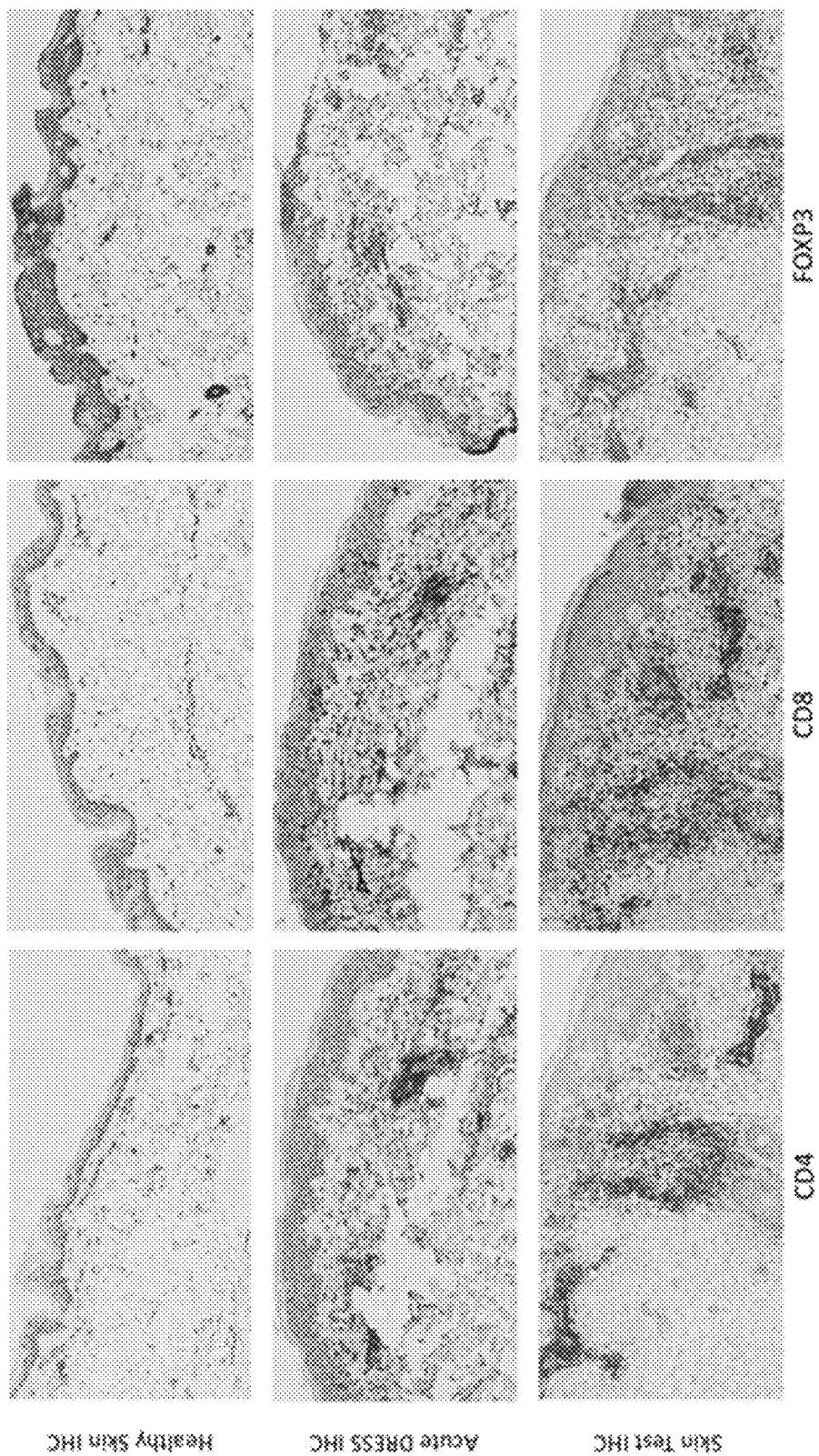

Vancomycin intradermal testing (IDT) produced strong immediate histamine responses at 20 minutes in both HLA-A*32:01 positive individuals who were tested, but only the patient with a history of DRESS developed a delayed positive IDT with dermal induration and erythema at vancomycin concentrations of 0.5, 5 and 50 mg/mL recorded 24 and 48 hours after drug placement (FIGS. 3A and 3B). In addition, patient 18 had negative immediate testing, delayed IDT and oral challenge to levofloxacin which had been co-administered with vancomycin. H&E staining from skin biopsies obtained from patient 18 from the acute DRESS reaction and the 5 mg/ml vancomycin positive IDT skin test showed the papillary dermal edema, epidermal spongiosis and dense lymphocytic infiltrate classically seen in DRESS histology (FIGS. 3C and 3D). Immunohistochemistry of these same biopsies showed no appreciable difference in the distribution of CD4 and CD8 positive cells in the dermal infiltrate between the acute and skin test biopsies. The acute biopsy did, however, demonstrate a substantially higher number of intraepidermal CD8+ T cells when compared to the skin test biopsy. Conversely, dermal FOXP3+T regulatory cells were present in the skin test biopsy but absent in the acute biopsy (FIG. 3E).

Molecular Docking of Vancomycin with HLA-A*32:01

Molecular docking was used to estimate potential interactions between vancomycin and HLA-A*32:01. A homology model of peptide/HLA-A*32:01 complex was generated based on the most similar solved structure (PDB 6EI2, HLA-A68, 92% identical) and used AutoDock Vina to predict binding orientations and scores. Vancomycin was not predicted to bind HLA-A*32:01 with high affinity when peptide occupied the antigen binding cleft (ΔG=−7.3 kcal/mole) (RLYGKSLYSF, corresponding to a peptide eluted from HLA-A*32:01). However, vancomycin was predicted to bind the antigen binding cleft of HLA-A*32:01 with higher affinity in the absence of peptide, ΔG=−7.7 kcal/mole (FIG. 4). These data suggest that vancomycin has the potential to bind within the antigen binding cleft of HLA-A*32:01 in the absence of peptides that conform to the canonical HLA-A*32:01 binding motif (9mer P1 K or R, PΩ F, I or L)[18].

Vancomycin was predicted to bind antigen binding cleft residues in HLA-A*32:01 that differ between closely related alleles not associated with vancomycin induced DRESS, such as HLA-A*29:02 (polymorphic differences shown in magenta in FIG. 4). Since the on-target mechanism of action for vancomycin is binding D-Ala-D-Ala in the bacterial cell wall, the potential of vancomycin to bind consecutive alanine residues in HLA-A*32:01 was explored.

Molecular docking suggests that vancomycin is not likely to bind consecutive alanine residues (L isomers) in HLA-A*32:01. The top scoring molecular docking orientation shows that the vancomycin atoms contacting D-Ala-D-Ala were predicted to bind HLA-A*32:01 in the central region of the cleft normally occupied by the central positions in peptide backbone (shown in cyan in FIG. 4).

Discussion

The international implementation of routine preprescription screening for HLA-B*57:01 has eliminated abacavir hypersensitivity as a clinical entity and has paved the way for the translation of other HLA screening strategies for the prevention of drug hypersensitivity reactions into clinical practice[7-8, 19-20]. Similar to the discovery of abacavir and HLA-B*57:01, the study highlights the utility of using large clinical databases and prospectively defined cases in combination with adjunctive immunological information to define genetic associations with a specific clinical phenotype[7-8, 21]. Since vancomycin is frequently prescribed empirically in an urgent manner for acute life-threatening infections, unlike previous models that suggest HLA screening prior to intended prescription of a drug, use of HLA-A*32:01 typing may be more appropriate following initiation of vancomycin, when bacterial culture information is available, and in patients destined to receive longer or multiple treatment courses to identify those that could be at risk for vancomycin DRESS. This would be facilitated through the development of a single allele assay for HLA-A*32:01, similar to approaches developed for HLA-B*57:01 and HLA-B*15:02, which are now widely available through commercial laboratories with short turnaround times. Since the cohort was of predominantly European ancestry, further studies will be needed to exclude the possibility that HLA alleles other than HLA-A*32:01 are associated with vancomycin DRESS in other ethnic groups. The time-to-event analysis suggests that the risk of DRESS approaches 20% at four weeks of therapy in those carrying HLA-A*32:01, but those tolerant to vancomycin at 4 weeks are likely at low risk of DRESS thereafter (FIGS. 2 and 4).

Ex vivo and in vivo diagnostic approaches such as IFNγ ELISpot assays and IDT warrant further study for their sensitivity, specificity and safety for vancomycin and concurrently administered medications[22]. In patient 18, evidence of a localized DRESS reaction on histopathology from a positive IDT biopsy demonstrates that the immunopathology of the acute reaction can be recapitulated in the skin following disease recovery. Consistent with previous studies showing that the ratio of FOXP3+ T cells to overall CD3+ T cells in acute DRESS skin positively correlates with longer times from start of symptoms to skin biopsy, an increase is FOXP3+ regulatory T cells was observed in the dermis of recovery phase skin following intradermal vancomycin administration (FIG. 3E)[23]. This also suggests that regulatory T cells may reside in the skin weeks to months following acute DRESS.

Vancomycin has been associated with other ADRs including linear IgA bullous dermatosis, fixed drug eruption, acute generalized exanthematous pustulosis, and Stevens-Johnson syndrome/toxic epidermal necrolysis[1,24]. Ten (10) individuals with non-DRESS vancomycin immune-mediated adverse drug reactions were enrolled in the broader drug hypersensitivity studies. Only 1/10 is HLA-A*32:01 positive which suggests that this association is specific for vancomycin DRESS and that HLA screening would not prevent other vancomycin-induced delayed hypersensitivity reactions.

Although the specific mechanism of vancomycin DRESS is unknown, the data may provide clues to the immunopathogenesis of this syndrome. The strong association with HLA-A*32:01 supports that vancomycin DRESS is an HLA Class I-restricted, CD8+ T-cell mediated process. For the HLA-B*57:01-restricted abacavir hypersensitivity reaction, immunologically-confirmed hypersensitivity can occur as early as 1.5 days of first dosing suggesting that a pre-existing memory T-cell response may be mechanistic[8]. In contrast, vancomycin DRESS in ours and other studies is characterized by a long latency period (median 21 days)[25]. Further, HLA-A*32:01 positive individuals who have not been exposed to vancomycin were observed to have negative responses to vancomycin by both in vivo (intradermal challenge) and ex vivo (IFNγ ELISpot) assessments. These data might suggest that vancomycin DRESS pathogenesis is dependent upon a naïve T-cell response requiring CD4+ T-cell help. Vancomycin is a large glycopeptide and is excreted unchanged in the urine. Unlike abacavir which has been shown to alter the repertoire of self-peptides presented to T cells in HLA-B*57:01 positive individuals[26-27], the model suggests that vancomycin may bind within the antigen binding cleft of HLA-A*32:01 in the absence of peptides that conform to the canonical HLA-A*32:01 binding motif (FIG. 4).

Currently, the use of HLA testing in clinical practice has been limited to preprescription screening strategies. This discovery of a strong association between HLA-A*32:01 and one of the most serious immunologically-mediated reactions associated with a commonly used antibiotic, vancomycin, raises the possibility that HLA testing could be used as a diagnostic risk stratification tool after initiation of vancomycin treatment but prior to development of vancomycin DRESS. Patients with complex and life-threatening infections commonly receive vancomycin dosed concurrently with beta-lactams or fluoroquinolone antibiotics as was noted in 21/23 (91%) of the cases. This often leads to patients with DRESS being labeled as allergic to all of these antibiotic classes, which significantly restricts current and future treatment options. In those found to be HLA-A*32:01 positive, vancomycin treatment could either be rationalized where therapeutically appropriate or continued under close clinical observation and laboratory monitoring with discontinuation of vancomycin at the first sign of early DRESS symptoms. Alternatively, for those who develop possible vancomycin-induced DRESS or who have a known history suggestive of vancomycin DRESS, HLA-A*32:01 testing could be combined with adjunctive testing such as IFNγ ELISpot to vancomycin and other co-administered drugs to improve drug causality assessment. These strategies have the immediate potential to improve patient care by improving drug safety, increasing short-term drug efficacy and reducing future constriction of antibiotic choices.

Materials & Methods

DNA Samples. For this study, 458 DNA samples drawn from the BioVU/VESPA cohort[38] were analyzed by AS-PCR/melting curve. These DNA samples had previously undergone high resolution, full allelic HLA typing by next generation sequencing and in depth genotyping with structured race assignment[9]. DNA sample identity was blinded to the operator at the time of the validation of the assay. The DNA samples were of good quality with a mean DNA concentration of 50 ng/ul and a 260/280 ratio over 1.7. For this assay, the DNA concentration of samples were normalized to a concentration of 25 ng/ul with sterile deionized water (Sigma, Cat #W3500). The study sample contained a good representation of the HLA-A*32:01 allele (n=30) with a broad range of HLA-A*32-closely related alleles as listed in Table 6.

TABLE 6

HLA genotypes of samples eliminated by the present assay (HLA-A*32:01 AS-PCR)

| HLA-A specificities | Number |
|---|---|
| A*01:01 | 123 |
| A*02:01, A*02:05 | 202 |
| A*11:01 | 45 |
| A*23:01 | 9 |
| A*24:02 | 41 |
| A*25:01 | 12 |
| A*26:01 | 18 |
| A*29:02 | 28 |
| A*30:01 | 21 |
| A*31:01 | 31 |
| A*33:01 | 7 |
| A*66:01 | 2 |
| A*68:01, A*68:02 | 49 |

Primers. Primers (shown in Table 7) were designed within the exon 2 of HLA A locus. HLA-A sequences from IMGT/HLA database were aligned with HLA-A*01:01:01 using CLCGenomics Workbench 9.0.1 (Qiagen, USA). Primers were designed to specifically amplify HLA-A*32 alleles (FIG. 1). HLA-A*32 AS-PCR was performed using a combination of a locked nucleic acid (LNA) forward primer with a standard reverse primer. The LNA primer was designed to be locked at the T nucleotide and thus to uniquely target HLA-A*32 alleles, yielding a 157-bp product. Internal control primers were designed to amplify the highly conserved housekeeping gene galactosylceramidase (GALC), yielding a 352-bp product.

TABLE 7

Primer sequences for HLA typing of HLA-A*32:01 allele.

| Primer name | Description | Sequence (5' to 3') | Target |
|---|---|---|---|
| HLA 32-88F | HLA-A*32 forward primer | GACGACACGCAGTTCGT GCGGTT+T | HLA-A*32 |
| HLA 032R2 | HLA-A*32 reverse primer | GAGCGCGATCCGCAGGC | HLA-A*32 |
| GALC-F: | GALC forward primer | TTACCCAGAGCCCTATCG TTCT | GALC |
| GALC-R: | GALC reverse primer | GTCTGCCCATCACCACCT ATT | GALC |

Allele-Specific PCR for Detection of HLA-A*32:01. The real-time PCR reaction contained 2 ul (50 ng) of total DNA, 1× Power Up SYBR Green Master Mix (Thermo Fisher Scientific, Australia), 250 nM of each HLA-A*32 specific primer, and 50 nM of each GALC primer in a 10-μl final volume. The master mix was dispensed on a 96 or 384-well qPCR plate using the Mantis® Liquid Handler (Formulatrix®, Massachusetts, USA) by using a high-volume chip. DNA samples were stamped on a 96- or 384-well qPCR plate straight from the DNA storage plates using the Biomek® FXP liquid handler (Beckman Coulter, Australia) The real-time PCR was performed in 96-well or 384 well optical plates on Bio-Rad CFX96/384 qPCR machine (Bio-Rad, Australia) using the following cycling conditions: Initial denaturation at 96° C. for 6 min to allow polymerase activation, followed by 35 cycles at 96° C. for 30 seconds and 62° C. for 1 minute. This was followed by a melting curve cycle from 65° C. to 95° C. with 0.5° C. increment for 5 seconds. The conditions of the PCR, such as primer concentrations and cycling conditions, were optimized to enable a clear separation of both HLA-A*32 specific Tm peak compared to the internal control Tm peak during melt curve analysis.

A standard AS-PCR was performed using the same reactions conditions as for the real-time PCR. The standard AS-PCR was performed in 96-well half skirt PCR plates (AXYGEN Scientific, Australia) on the Bio-Rad C1000 thermocycler (Bio-Rad Laboratories, Australia). PCR products were analyzed by electrophoresis on a 1% agarose gel containing 0.2 μg/ml ethidium bromide and run at 115V for 30 minutes at room temperature. The gel was visualized by a transilluminator (ChemiDoc XRS+, Bio-Rad, Australia).

Data Analysis. Raw real-time PCR data were analyzed using CFX Manager Software 3.0 (Bio-Rad, Australia). Statistical analyses for validation studies to calculate sensitivity, specificity, and confidence intervals were performed using GraphPad Prism 5.02 for Windows (GraphPad Software Inc., San Diego, California, USA).

Results

To validate this HLA-A*32:01 typing assay, 458 samples previously typed using American Society for Histocompatibility and Immunogenetics (ASHI) accredited sequence-based high-resolution, full allelic HLA typing were analyzed using the real-time PCR with Power Up SYBR Green master mix. All thirty samples out of the 458 samples were accurately identified as positive for HLA-A*32:01 allele.

Samples were called positive or negative for HLA-A*32:01 based on the presence or absence the HLA-A*32:01 specific melt peaks. HLA-A*32:01-positive samples (n=30) showed two peaks at 88.5° C.±0.0° C. (mean±standard error of the mean; range: 88.50° C.-88.50° C.) for the HLA-A*32:01 allele and 76.05° C.±0.03° C. (mean±standard error of the mean; range: 76.00° C.-76.50° C.) for GALC. The other 428 non-HLA-A*32 samples showed a single peak at 76.07° C.±0.01° C. (mean±standard error of the mean; range: 75.50° C.-76.50° C.) for GALC (FIG. 2). No melting curves were detectable for the non-template negative controls (Table 8).

TABLE 8

Melting curve analysis of HLA-A*32:01 and GALC amplicons.

| | Tm peaks | | Amplicon length | |
|---|---|---|---|---|
| HLA allels | HLA-A*32:01 | GALC | (bp) | Validation |
| HLA-A*32:01 | 88.5 | 76 | 157 | Positive |
| Non-HLA-A*32 | None | 76 | 352 | Negative |

Tm: melting point;
GALC: galactosylceramidase;
bp: base pairs

For the standard AS-PCR, samples were called positive or negative based on the presence or absence of the HLA-A*32:01 specific PCR product after agarose gel electrophoresis. HLA-A*32:01 positive samples showed two bands of 157-bp (HLA-A*32:01) and 352-bp (GALC). Non-HLA-A*32 samples showed only one band of 352-bp (GALC) (FIG. 2). No product was detectable for the non-template negative controls. Thus, the sensitivity and specificity of this assay for HLA-A*32:01 allele in these 458 DNA samples were 100% (95% CI: 88.43-100%) and 100% (95% CI: 99.14-100%) respectively (Table 9).

TABLE 9

Comparison of the present assay with SBT.

| HLA-A*32;01 gPCR | HLA SBT | | |
|---|---|---|---|
| | HLA-A*32 | Non-HLA-A*32 | Total |
| Positive | 30 | 0 | 30 |
| Negative | 0 | 428 | 428 |
| Total | 30 | 428 | 458 |

Discussion

This study describes a simple, fast, and inexpensive PCR assay that utilizes AS-PCR with melt curve analysis for the detection of HLA-A*32:01 allele. By using a combination of primers that included a LNA forward primer, the HLA-A*32:01 allele was specifically amplified in a real-time PCR. The assay was both 100% sensitive and specific making it safe and appropriate for clinical use.

Amplification of low-level nonspecific products in real-time PCR has been previously reported. The formation of these nonspecific products can be influenced by annealing temperature, primer concentration, magnesium concentration, and DNA inputs 39. In this optimized assay, no evidence of non-specific amplification was detected. It is also worth noting that in the experiments a LNA primer that specifically target the HLA-A*32 allele was used. The incorporation of a LNA primer into oligonucleotide primers provides an increase of specific binding strength for target DNA amplification[40]. A commercial optimized real-time PCR master mix (Power Up SYBR Green master mix) was used, which is reported to be formulated for maximum specificity and reproducibility. The detection range for template DNA in the assay was between 10 ng to 100 ng. However, the assay optimal DNA concentration was between 25 ng and 50 ng.

The specificity of the assay was assessed for only the HLA-A*32:01 allele.

Given the low frequency of other HLA-A*32 alleles (e.g. A*32:02, A*32:03) especially in those of European ancestry[41] (www.allelefrequencies.net, last accessed on 15 Jan. 2019), there were not other non-HLA-A*32:01 alleles identified from the biorepository of samples primarily from those of European ancestry. Notably, across the entire Vanderbilt BioVU cohort with imputed HLA typing (N=65,638), the only HLA-A*32 allele imputed was HLA-A*32:01. European ancestry represented 85% of this cohort. Furthermore, it is currently unknown whether HLA-A*32 alleles other than HLA-A*32:01 are associated with vancomycin DRESS or whether there are associations between other HLA alleles and vancomycin DRESS in those of non-European ancestry. This will be important to clarify as for previous associations between drug hypersensitivity and HLA alleles such as abacavir and HLA-B*57:01, an allele also primarily represented in those of European ancestry, the association was specific for HLA-B*57:01 and to-date HLA-B*57:01 screening has a 100% negative predictive value for abacavir hypersensitivity. Alleles such as HLA-B*58:01, HLA-B*57:03 and HLA-B*57:02 which differ by as few as 2 amino acids in the antigen binding cleft are not associated with abacavir hypersensitivity[8]. HLA-A*32:01 has a leucine at position 156 which is a key peptide binding residue which differs from the glutamine at 156 for HLA-A*32:02 and HLA-A*32:03 (IPD-IMGT/HALA database; www.ebi-.ac.uk/cgi-bin/ipd/imgt/hla/align.cgi; last accessed on 4 Jan. 2019). It is also worth noting that this assay was able to exclude closely related non-HLA-A*32 alleles.

High resolution HLA typing is performed by direct sequencing of HLA class I and class II sequences. Although sequence-based typing (SBT) remains the gold standard for HLA typing, it is significantly more expensive, requires significant expertise and labor and has a longer turnaround time compared to this assay in terms of time, cost and labor and remains the domain of specialty immunogenetics and transplant laboratories. SBT also requires sophisticated equipment, highly-trained staff, and a robust informatics and quality assurance infrastructure which might not be available in most of clinical settings. HLA typing by hybridization of PCR amplicon with sequence-specific oligonucleotide probes (SSO) is an alternative method, but this method shows low resolution typing 42.

The assay described here appears to give both specificity and sensitivity of 100%, with the advantage of being very fast and less costly compared to other HLA typing methods. The flexible methodology means that this could be set-up in a variety of specialty immunogenetics or non-specialty laboratory settings that have access to a PCR platform that can perform melting curve analysis. Those settings without qPCR platform can use the standard AS-PCR followed by agarose gel electrophoresis. Limited testing was conducted on a standard PCR machine with the Power Up SYBR green master mix followed by agarose gel electrophoresis analysis and gel visualization. It was also found that this assay can be successfully adapted in settings which do not have qPCR platform.

The considerable reduction of operator manual handling of post PCR amplicon and manipulation of results also reduce the potential risk of sample mix-up as well as contamination. Where testing a large number of samples is needed, the use of robotic liquid handling system for transferring master mixes and DNA samples could provide some benefits in reducing turnaround time and human errors. In cases where unusual melt curves are found due to poor purity of DNA or operator technical error, samples should be further evaluated by using conventional PCR genotyping or SBT or by obtaining another sample. However, such cases were not encountered during the validation experiments.

Currently single allele assays exist or have been published for HLA-B*57:01, HLA-B*15:02, HLA-B*58:01 and HLA-A*31:01[43-47] Most of these single allele assays have been advocated as a pre-prescription screening strategy with specific drugs and specific populations[48, 49].

The study is therefore novel in both reporting both a new single-allele test specific for HLA-A*32:01 and also in proposing a new use approach to pharmacogenetic testing that is practical and convenient for both the clinician and the laboratory. Based on a prevalence of HLA-A*32:01 in a population of predominant European ancestry of 6.8% and estimates from the published paper that approximately 20% of those carrying HLA-A*32:01 exposed to vancomycin for at least 2 weeks will develop vancomycin DRESS, it can be estimated that 75 patients would need to be tested for HLA-A*32:01 to prevent one case of DRESS. Given the low cost and relative convenience of testing in this clinical context and the severe implications of DRESS, this number needed to test should be sufficient to justify testing from a cost-effectiveness standpoint in most populations with carriage frequencies of HLA-A*32:01 similar to ours. Furthermore, it would also be feasible, to use this rapid turn-around single-allele assay turnaround, as an ancillary diagnostic test in patients who have developed DRESS on multiple antibiotics including vancomycin.

In conclusion, this AS-PCR is a fast and reliable method for typing the HLA-A*32:01 allele. This assay demonstrates the sensitivity and specificity needed for the assignment of the HLA-A*32:01 allele but caution that these assay characteristics may not be maintained with any modification to the method.

Example 2

Figure 10:
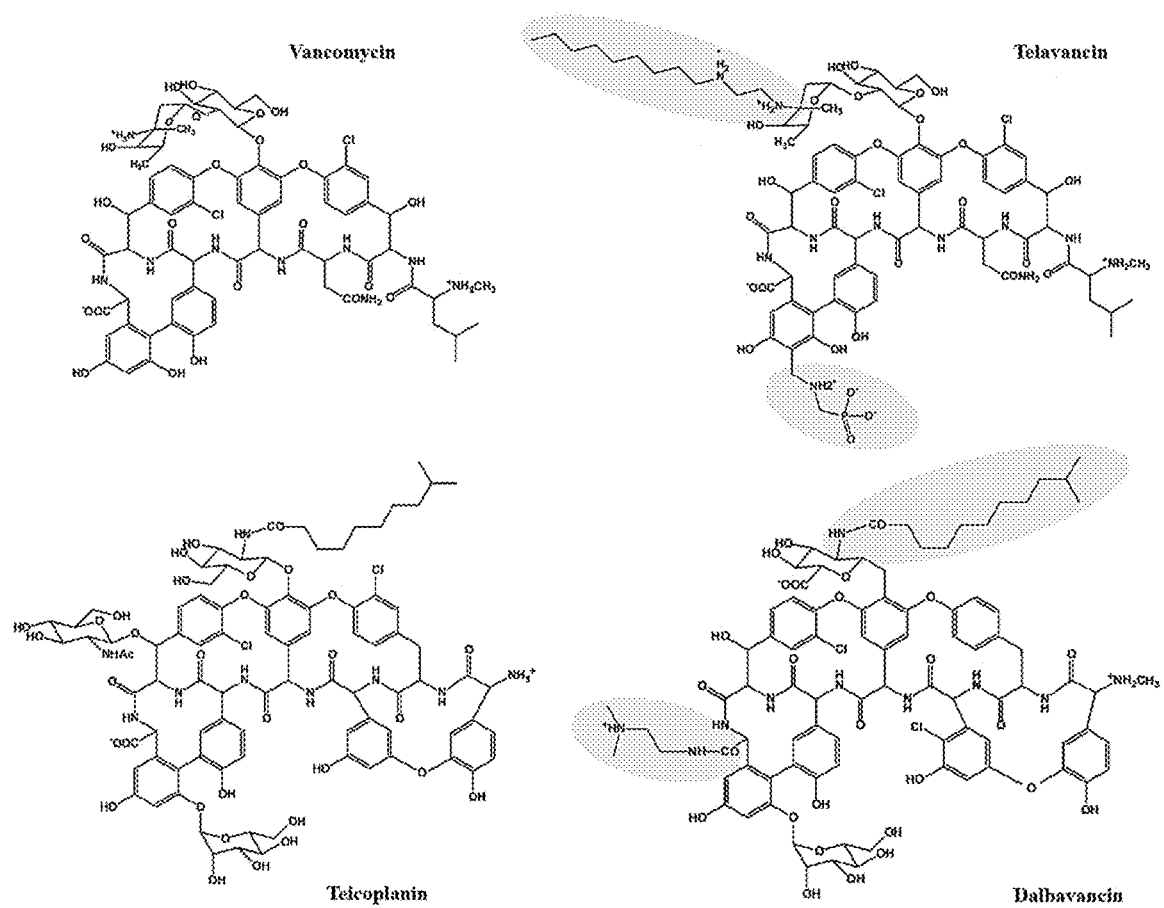
FIG. 10: Chemical structures of vancomycin, telavancin, teicoplanin and dalbavancin. Vancomycin and teicoplanin are the first generation of clinically important glycopeptide antibiotics. Dalbavancin is a semisynthetic lipoglycopeptide which is a derivative of the teicoplanin-like A40926. Telavancin is a newer semisynthetic lipoglycopeptide, a derivative of vancomycin.

Utilizing a population of patients with HLA-A*32:01 positive vancomycin DRESS (vancomycin IFN-γ release Enzyme-Linked ImmunoSpot (ELISpot) Assay positive and RegiSCAR≥4), the immunological cross-reactivity amongst four glycopeptide antibiotics was examined, including vancomycin, teicoplanin, dalbavancin, and telavancin in patients.[1] The chemical structures of vancomycin, telavancin, teicoplanin and dalbavancin are shown in FIG. 10.

Adults 18 years or older with a probable diagnosis of vancomycin DRESS defined by a corresponding Naranjo adverse drug reaction (ADR) score of ≥5 (probable ADR), a RegiSCAR score of ≥4 (probable DRESS) and who carried HLA-A*32:01 were recruited through drug allergy clinics and inpatient facilities at participating institutions (Vanderbilt University Medical Center in Nashville, Tennessee; Austin Health, Peter MacCallum Cancer Centre, Fiona Stanley Hospital and Royal Perth Hospital in Perth, Western Australia, Australia). All patients provided written or electronic informed consent. Saliva and blood were collected, processed, and stored as repositories of DNA, peripheral blood mononuclear cells (PBMCs), and plasma.

Figure 11:
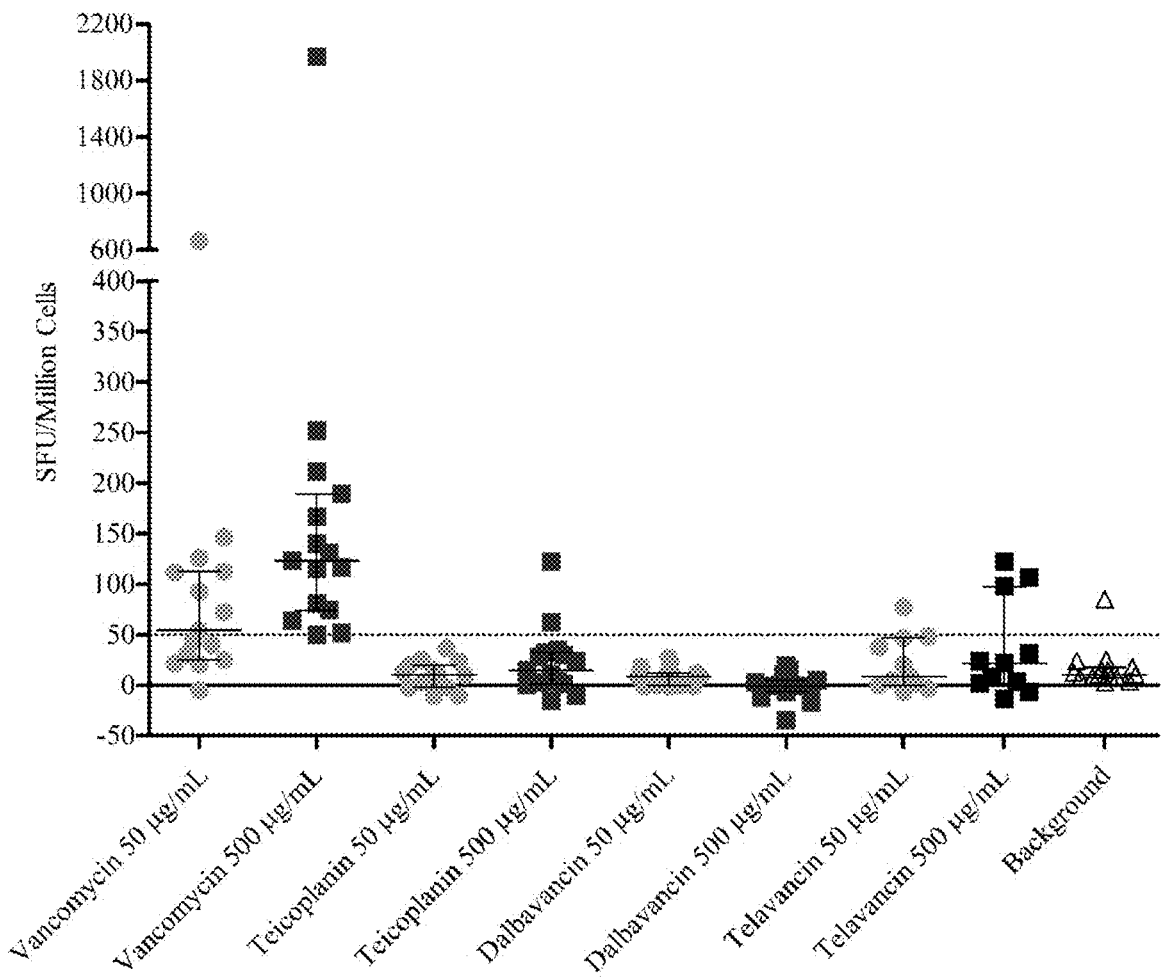
FIG. 11. IFN-γ release ELISpot results using PBMCs from 15 potential vancomycin DRESS patients after 20 hours of incubation with vancomycin, teicoplanin, dalbavancin, and telavancin (Telavancin stimulation was tested on 11 cases). Means of the triplicates are plotted. Error bars indicate interquartile range of the median ELISpot results from all cases after background subtraction. A positive response was defined as >50 SFU/million cells after background removal. Two patients (Patient ID 8 and 15) showed cross-reactivity between vancomycin, teicoplanin and telavancin and one patient (Patient ID 7) showed potential cross-reactivity between vancomycin and telavancin at 500 µg/mL (see Table 12 for details).

IFN-γ release in response to overnight incubation with the implicated drugs was performed by ELISpot assay) 3420-2H; Mabtech, Stockholm, Sweden (in triplicate from thawed PBMCs) rested overnight (and included negative) unstimulated (and positive) anti-CD3 Mabtech antibody, staphylococcal enterotoxin B, and/or cytomegalovirus pp65 (controls. Control PBMCs from glycopeptide unexposed HLA-A*32:01 positive and negative individuals were also used. PBMCs plated at 200,000 cells/well were incubated with vancomycin, teicoplanin, dalbavancin, telavancin and other implicated drugs at concentrations representative of maximum serum concentrations, as well as those 10-fold higher and 10-fold lower (FIG. 11). A positive response was defined as more than 50 spot-forming units (SFU)/million cells after background removal as per previous definitions.[12] High-resolution 4-digit HLA-A, HLA-B, HLA-C, HLA-DP, HLA-DR, and HLA-DQ typing was performed by using sequence-based typing with previously published protocols.[31]

Fifteen patients who met the clinical inclusion criteria for vancomycin-induced DRESS syndrome were enrolled into this study. These patients were primary European ancestry and included 10 women and 5 men from 26 to 76 of age. The median latency period from vancomycin initiation to the first symptoms of DRESS was 21 days (interquartile range (IQR), 15.5-26.5 days). The demographics, clinical characteristics, and DRESS history are described in Table 10. Full HLA typing of all cases are presented in Table 11.

TABLE 10

The demographics, clinical characteristics, and DRESS history.

| ID | Age (years) | Sex | Race | Latency (days) | Regi-SCAR | Naranjo score | Indication of vancomycin | Other potentially implicated medications |
|---|---|---|---|---|---|---|---|---|
| 1 | 53 | F | White | 23 | 7 | 8 | Culture-negative soft-tissue infection with underlying rib osteomyelitis | Levofloxacin, fluconazole |
| 2 | 38 | M | White | 18 | 5 | 8 | MRSA right chest phlegmon, deep soft-tissue infection, underlying osteomyelitis of second rib with fracture | Rifampin |
| 3 | 47 | F | White | 17 | 6 | 8 | MRSA and Escherichia coli bacteremia with chest infiltrate | Levofloxacin |
| 4 | 61 | F | White | 50 | 5 | 8 | MRSA wound infection leading to hip prosthesis removal and placement of vancomycin spacer | Ciprofloxacin |
| 5 | 59 | F | White | 34 | 5 | 6 | Complex ocular infection | Benzyl penicillin |
| 6 | 62 | F | White | 24 | 7 | 5 | Cellulitis (soft tissue) | Ceftazidime |
| 7 | 69 | F | White | 16 | 7 | 6 | MRSA wound infection | None |
| 8 | 40 | F | White | 14 | 4 | 6 | E. faecalis pyelonephritis | Ceftriaxone |
| 9 | 45 | F | White | 11 | 6 | 8 | Ventriculitis - empirical. Culture negative | Ceftazidime |
| 10 | 47 | F | White | 15 | 5 | 6 | Ventriculitis - empirical. Culture negative | Cefepime |
| 11 | 38 | F | White | 12 | 7 | 6 | Post cardiac surgery wound infection-culture negative | None |
| 12 | 76 | M | White | 27 | 6 | 8 | Enterococcus species bacteremia and endocarditis | Gentamicin, benzylpenicillin |
| 13 | 66 | M | White | 21 | 4 | 8 | MRSA osteomyelitis | Rifampin |
| 14 | 29 | M | White | 26 | 5 | 8 | Traumatic arm injury and possible osteomyelitis | Trimethoprim/sulfamethoxazole, piperacillin-tazobactam, ciprofloxacin |
| 15 | 37 | M | White | 28 | 5 | 8 | Skin and soft tissue infection - MSSA | Ceftriaxone |

TABLE 10-continued

The demographics, clinical characteristics, and DRESS history.

| ID | Immunosuppression | Peak Liver Enzymes >2x Normal (Y/N) | Peak Creatinine (mg/dL) | Time from original reaction to ex vivo testing (days) |
|---|---|---|---|---|
| 1 | Prednisone | Y | 1.44 | 217 |
| 2 | Prednisone | N | 1.12 | 151 |
| 3 | Prednisone | Y | 0.71 | 285 |
| 4 | Prednisone | Y | 5.12 | 21 |
| 5 | Prednisone | N | 1.41 | 3 |
| 6 | Prednisone | Y | 6.74 | 4 |
| 7 | Renal dialysis patient | Y | 10.81 | 209 |
| 8 | Pregnancy | Y | 1.39 | 13 |
| 9 | None | Y | 0.81 | 5 |
| 10 | None | Y | 0.58 | 429 |
| 11 | Severe diabetes | N | 2.90 | 1202 |
| 12 | High dose steroids | Y | 6.19 | 178 |
| 13 | None | Y | 1.38 | 3018 |
| 14 | None | Y | 2.24 | 834 |
| 15 | None | Y | 1.14 | 99 |

The length of the steroid tapers ranged from 4 weeks to >6 months.
Data in quotes were taken directly from the electronic health records when laboratory values or medication records were not available.
Where relevant creatinine values have been converted from μmol/L to mg/dL.
Legend:
Y, yes;
N, No.

TABLE 11

Full HLA typing results of potential vancomycin DRESS patients

| ID | HLA-A Allele 1/2 | HLA-B Allele 1/2 | HLA-C Allele 1/2 | HLA-DPB1 Allele 1/2 | HLA-DQA1 Allele 1/2 | HLA-DQB1 Allele 1/2 | HLA-DRB1 Allele 1/2 |
|---|---|---|---|---|---|---|---|
| 1 | 03:01/32:01 | 07:02/18:01 | 07:02/07:41 | 03:01/04:01 | NT | 02:01/06:02 | 03:01/15:01 |
| 2 | 03:01/32:01 | 07:02/07:02 | 07:02/07:02 | 03:01/04:01 | 01:02/03:01 | 03:01/06:02 | 04:07/15:01 |
| 3 | 03:01/32:01 | 07:02/14:01 | 07:02/08:02 | 02:01/05:01 | 03:01/03:01 | 03:02/03:02 | 04:04/04:04 |
| 4 | 68:01/32:01 | 13:02/51:01 | 02:02/06:02 | 02:01/04:01 | 02:01/03:01 | 02:02/03:03 | 07:01/09:01 |
| 5 | 01:01/32:01 | 44:02/44:02 | 05:01/05:01 | 04:02/13:01 | 02:01/03:01 | 03:01/03:03 | 04:01/07:01 |
| 6 | 02:01/32:01 | 44:02/45:01 | 05:01/06:02 | 04:01/04:01 | 01:02/03:01 | 03:01/06:04 | 04:01/13:02 |
| 7 | 03:01/32:01 | 35:01/40:02 | 02:02/04:01 | 03:01/04:01 | 05:01/05:01 | 03:01/03:01 | 11:01/11:01 |
| 8 | 03:01/32:01 | 15:01/44:02 | 03:04/05:01 | 02:01/11:01 | 01:01/02:01 | 02:02/05:03 | 07:01/14:01 |
| 9 | 32:01/32:01 | 50:01/50:01 | 06:02/06:02 | 04:01/04:01 | 02:01/02:01 | 02:02/02:02 | 07:01/07:01 |
| 10 | 24:02/32:01 | 08:01/40:01 | 03:04/07:01 | 02:01/04:02 | 03:01/05:01 | 02:01/03:02 | 03:01/04:04 |
| 11 | 01:01/32:01 | 07:02/44:02 | 05:01/07:02 | 02:01/04:01 | 01:02/01:03 | 06:02/06:03 | 13:01/15:01 |
| 12 | 01:01/32:01 | 13:02/51:01 | 06:02/14:02 | 01:01/04:01 | 02:01/02:01 | 02:02/02:02 | 07:01/07:01 |
| 13 | 01:01/32:01 | 08:01/44:02 | 05:01/07:01 | 04:01/19:01 | NT | 05:03/06:02 | 14/15 |
| 14 | 23:01/32:01 | 44:02/49:01 | 05:01/07:01 | 02:01/04:02 | 05:01/05:01 | 03:01/03:01 | 11:01/12:01 |
| 15 | 02:01/32:01 | 14:01/35:03 | 04:01/08:02 | 02:01/14:01 | 01:01/02:01 | 02:02/05:03 | 07:01/14:01 |

Figure 12:
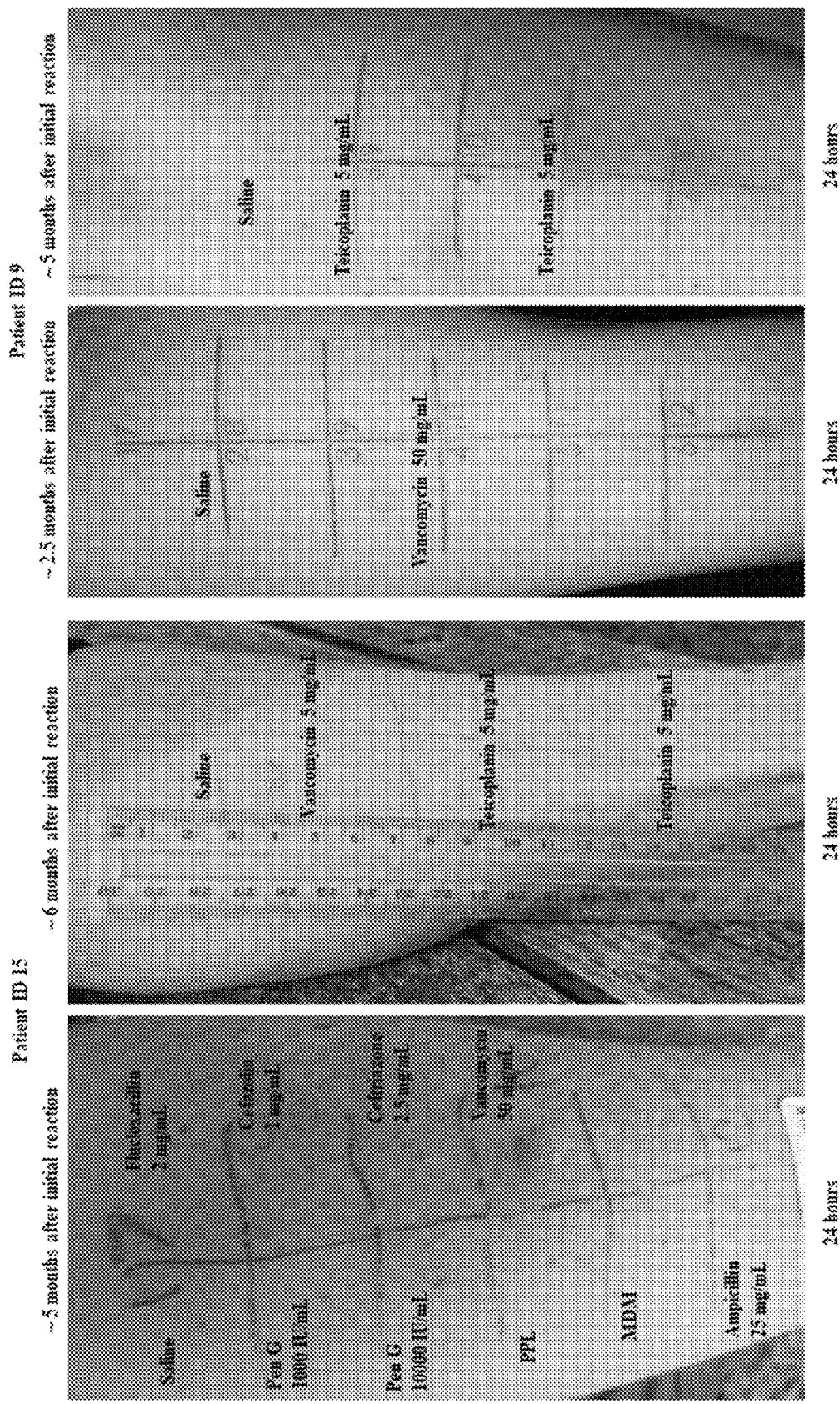
FIG. 12. Intradermal skin testing results. Patient ID 15 was skin tested intradermally to both vancomycin and teicoplanin approximately 6 months after vancomycin DRESS and showed positive responses to both vancomycin and teicoplanin. The skin testing results of Patient ID 15 were consistent with the IFN-γ ELISpot response to both drugs. Patient ID 9 showed positive delayed intradermal testing and IFN-γ ELISpot to vancomycin but negative IFN-γ ELISpot and intradermal testing to teicoplanin. Legend: ID, patient identification; Pen G, Penicillin G; PPL, Penicilloyl-polylysine; MDM, Minor determinant mixture.

PBMCs from 15 (100%) vancomycin DRESS cases exhibited a positive IFN-γ ELISpot response to vancomycin in a dose dependent manner (50 μg/mL: median SFU/million cells [IQR], 54.17 [27.50-112.08] and 500 g/mL: median [IQR], 122.99 [77.50-177.92]) (FIG. 11, Table 12). All vancomycin IFN-γ ELISpot positive patients had a clear negative IFN-γ ELISpot response to both concentrations of dalbavancin (50 g/mL: median [IQR], 8.33 [0.00-11.25] and 500 μg/mL: median [IQR], −0.83 [−5.00-3.75]). PBMCs from 13/15 DRESS cases exhibited a negative IFN-γ ELISpot response to teicoplanin (50 μg/mL: median [IQR], 10.00 [0.08-17.50] and 500 μg/mL: median [IQR], 15.00 [1.67-31.25]). PBMCs from 2/15 cases showed a positive response to teicoplanin. Moreover, PBMCs from 6/9 vancomycin DRESS cases showed a negative IFN-γ ELISpot to telavancin (50 μg/mL: median [IQR], 8.30 [0.83-42.10] and 500 μg/mL: median [IQR], 21.67 [2.48-64.60]). There were three cases that demonstrated a positive IFN-γ ELISpot response to telavancin with 2/3 of these overlapping with the two cases who had a positive IFN-γ ELISpot response to both vancomycin and teicoplanin. One dually positive patient (Patient ID 15, Table 12) was intradermally skin tested to both vancomycin and teicoplanin and showed positive responses to both glycopeptides (FIG. 12) which was not seen in glycopeptide unexposed controls (n==5) and 3 patients (Patient ID 9, 10, and 11) with HLA-A*32:01 positive vancomycin DRESS who showed positive delayed intradermal testing and IFN-γ ELISpot to vancomycin but negative IFN-γ ELISpot and intradermal testing to teicoplanin. Patients ID 1,3 and 5 also tolerated ingestion challenges with concurrently administered medications.

TABLE 12

IFN-γ release ELISpot results using peripheral blood mononuclear cells from DRESS patients after overnight stimulation with four glycopeptide antibiotics at μg/mL concentrations.

| ID | Vanc 50 | Vanc 500 | Teico 50 | Teico 500 | Dalba 50 | Dalba 500 | Tela 50 | Tela 500 | Background |
|----|---------|----------|----------|-----------|----------|-----------|---------|----------|------------|
| 1  | 54.17   | 80.83    | 12.50    | 0.83      | 10.83    | 2.50      | N/A     | N/A      | 2.50       |
| 2  | 125.83  | 210.83   | 4.17     | 10.83     | 2.50     | −0.83     | N/A     | N/A      | 7.50       |
| 3  | 111.67  | 140.00   | 23.33    | 0.00      | 11.67    | −6.67     | 0.00    | −13.33   | 15.00      |
| 4  | 43.33   | 116.67   | 36.67    | 35.00     | 0.00     | 5.00      | N/A     | N/A      | 15.00      |
| 5  | 92.50   | 130.83   | −2.50    | 24.17     | −0.83    | 10.83     | −3.33   | 8.33     | 7.50       |
| 6  | 146.67  | 251.67   | 15.00    | −10.00    | 26.67    | −35.00    | 48.33   | 21.67    | 85.00      |
| 7  | −5.00   | 50.00    | 12.50    | 32.50     | −0.83    | −12.50    | 37.50   | 97.50    | 17.50      |
| 8  | 30.00   | 166.67   | 25.00    | 61.67     | 8.33     | 15.00     | 46.70   | 106.70   | 10.00      |
| 9  | 112.50  | 189.17   | 2.50     | 2.50      | 9.17     | −0.83     | 8.30    | 23.30    | 7.50       |
| 10 | 21.67   | 115.00   | 20.00    | 30.00     | 0.00     | −3.33     | 20.00   | 31.70    | 10.00      |
| 11 | 667.50  | 1965.00  | −10.00   | 15.00     | 0.00     | 0.00      | 5.00    | 3.30     | 25.00      |
| 12 | 72.41   | 122.99   | −10.34   | −14.94    | 10.34    | −17.24    | −6.67   | −6.67    | 24.14      |
| 13 | 39.68   | 51.35    | −2.33    | 28.01     | 18.67    | 0.00      | 1.67    | 1.67     | 7.00       |
| 14 | 20.53   | 64.01    | 3.62     | 3.62      | −1.21    | −1.21     | N/A     | N/A      | 3.62       |
| 15 | 25.00   | 74.17    | 10.00    | 122.50    | 22.50    | 19.17     | 77.50   | 122.50   | 12.50      |

A positive response was defined as >50 SFU/million cells after background removal.
Patient ID 8 and 15 showed cross-reactivity between vancomycin, teicoplanin and telavancin.
Patient ID 7 showed potential cross-reactivity between vancomycin and telavancin 500 μg/mL.
Legend:
ID, patient identification;
Vanc, vancomycin;
Teico, teicoplanin;
Dalba, dalbavancin,
Tela, telavancin.

Figure 13:
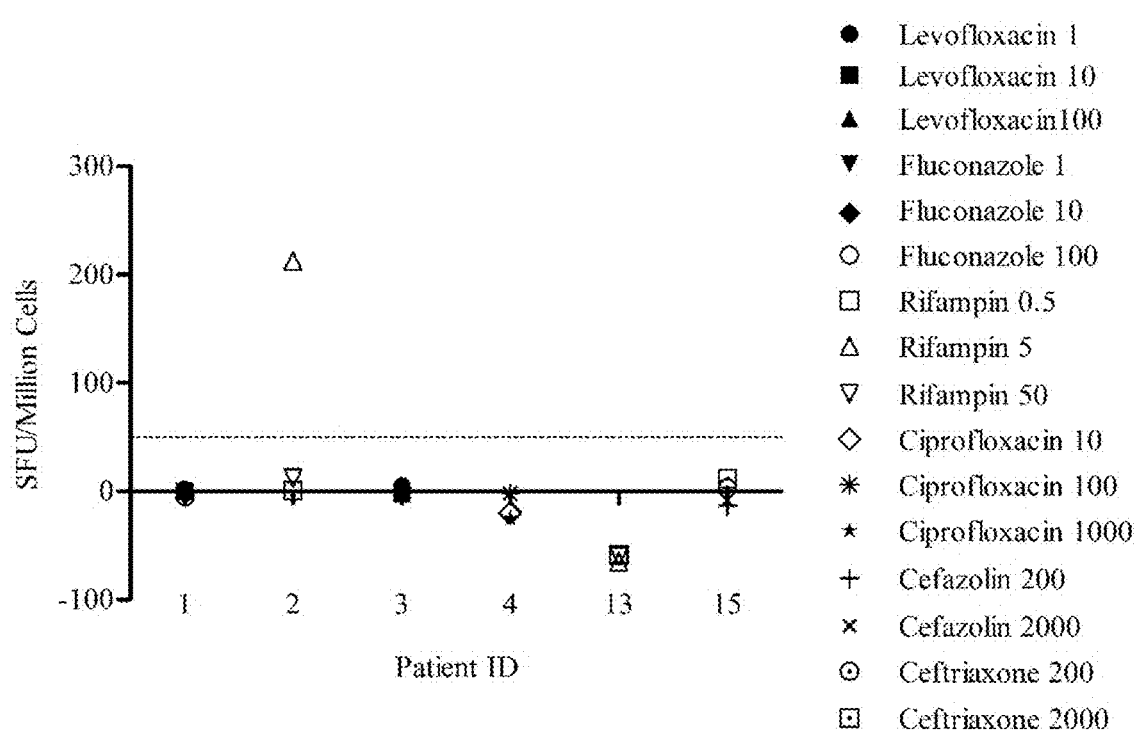
FIG. 13. IFN-γ release ELISpot results using peripheral blood mononuclear cells from DRESS patients after overnight stimulation with all medications taken concurrently with vancomycin. All drugs were tested at µg/mL concentrations. PBMCs from Patient ID 2 did respond to ex vivo vancomycin stimulation also had a positive response to rifampin at 5 µg/mL. However, PBMCs from Patient 13 and other healthy donors did not respond to rifampin stimulation. No other patient samples tested released IFN-γ in response to stimulation from any other medication. Means of the triplicates are plotted. Error bars indicate interquartile range of the median ELISpot results from all cases after background subtraction. A positive response was defined as >50 SFU/million cells after background removal. Legend: Patient ID, patient identification; SFU, spot-forming units.

In samples with sufficient cell number, PBMCs were tested against other concurrently administered medications potentially implicated in DRESS development. PBMCs from Patient ID 2 who did respond to ex vivo vancomycin stimulation also had a positive response to rifampin at only 5 μg/mL. No other patient samples tested released IFN-γ in response to stimulation from any other potentially implicated medication. (FIG. 13). Additionally, IFN-γ ELISpot was also performed on PBMCs from non-HLA-matched healthy donors (n=5) and a HLA-A*32:01 positive vancomycin naïve control (n=1); all exhibiting a negative response to all four drugs (data not shown).

Vancomycin is the most commonly used antibiotic and implicated in up to 40% of antibiotic-related DRESS cases. HLA-A*32:01 has recently been reported as a genetic risk factor for vancomycin-induced DRESS in the European population, within which the allelic prevalence is approximately 6.8%.[31] Due to the high prevalence of the risk allele, the high incidence of vancomycin-induced DRESS and the potential cross-reactive risk with dalbavancin given its extremely long half-life of 14 days, the detection of cross-reactivity to alternative glycopeptide antibiotics is very important for reducing the future risk of DRESS and providing patients with future therapeutic options. The study is reassuring in demonstrating that 100% of vancomycin DRESS cases with IFN-γ ELISpot responses showed a negative IFN-γ ELISpot response to dalbavancin, suggesting no or very low cross-reactivity between vancomycin and dalbavancin. Dalbavancin is a semisynthetic lipoglycopeptide, a derivative of the teicoplanin analogue A40926, and differs from vancomycin through a structural modification of the lipophilic side chain which enhances its binding affinity to the cell membrane and prolongs its half-life.[50]

On the other hand, approximately 87% (13/15) and 67% (6/9) of vancomycin DRESS cases showed no cross-reactivity to teicoplanin and telavancin, respectively. Interestingly, 13% (2/15) of vancomycin DRESS cases demonstrated immunological cross-reactivity to teicoplanin, and telavancin using ELISpot, confirmed in part by a positive intradermal skin test to teicoplanin in the one patient where this was performed (telavancin not available in clinical formulation for skin testing). It should be noted that telavancin is a direct semi-synthetic derivative of vancomycin and that dalbavancin is a semi-synthetic lipoglycopeptide derived from a glycopeptide structure more similar to teicoplanin. In addition to the long lipophilic side chain of dalbavancin that extends its half-life and improves affinity for the D-Ala-D-Ala target, dalbavancin lacks the acetyl-glucosamine group of teicoplanin. Intriguingly the two patients (Patient ID 8, 15) with shared ex vivo cross-reactivity amongst vancomycin, teicoplanin and telavancin share the same class II HLA haplotype which was distinct from the 13 patients who did not show ex vivo cross-reactivity with teicoplanin and telavancin.

Molecular docking suggests potential binding interactions between vancomycin, teicoplanin and telavancin and the class II HLA-DQA1*01:01 and HLA-DQB1*05:03 molecules in HLA-A*32:01 positive patients who have experienced vancomycin DRESS. These data suggest possible mechanisms including recognition of drug/class II HLA complexes by CD8 T cells matured by positive selection by HLA-A*32:01. The clinical phenotype in these cases with prior vancomycin DRESS and ex vivo cross-reactivity to teicoplanin and telavancin and positive delayed intradermal skin testing in the one patient performed could also be DRESS and so based on this a rechallenge to either teicoplanin or telavancin would not be ethical.

This study is the first evidence that elucidates a potential immunological cross-reactivity pattern amongst teicoplanin and newer glycopeptide antibiotics in patients with previous DRESS induced by vancomycin. Although this is reassuring, particularly for the use of the long half-life lipoglycopeptide dalbavancin, clinicians should be aware of the low but detectable risk of cross-reactivity in particular amongst teicoplanin, telavancin and vancomycin in the HLA-A*32: 01 restricted setting applicable to DRESS but also potentially other severe delayed reactions in teicoplanin- or telavancin-treated patients. Ideally both ex vivo IFN-γ ELISpot assay or skin tests in combination with HLA typing can be performed to risk-stratify patients with a history of previous vancomycin DRESS syndrome for potential risk of cross-reactivity between vancomycin, teicoplanin, and telavancin to aid in making decisions for future treatment. The shared class II haplotype amongst two patients with cross-reactivity between vancomycin, teicoplanin and dalbavancin and virtual docking of these drugs to HLA-DQA1*01:01 and HLA-DQB1*05:03 suggest a novel mechanism for cross-reactivity following sensitization that deserves further exploration.

Conclusions: Immunological cross-reactivity is demonstrable between vancomycin, teicoplanin and telavancin in patients with clinically and immunologically defined HLA-A*32:01 restricted vancomycin DRESS. Dalbavancin, a derivative of teicoplanin, showed little to no cross-reactivity highlighting it as the safest alternate glycopeptide. 22% of patients who demonstrated immunological cross-reactivity between vancomycin, teicoplanin, and telavancin shared a class II HLA haplotype, and drug class II structural modeling suggest a unique mechanism whereby HLA-A*32:01 restricted CD8+ T cells may recognize the neoepitope created by teicoplanin/telavancin HLA class II restricted CD4+ T cells.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Lin Y F, Yang C H, Sindy H, et al. Severe cutaneous adverse reactions related to systemic antibiotics. *Clin Infect Dis.* 2014; 58(10):1377-85.
2. Pavlos R, Mallal S, Phillips E. HLA and pharmacogenetics of drug hypersensitivity. *Pharmacogenomics.* 2012; 13(11):1285-1306.
3. Ghislain P D, Roujeau J C. Treatment of severe drug reactions: Stevens-Johnson syndrome, toxic epidermal necrolysis and hypersensitivity syndrome. *Dermatol Online J.* 2002; 8(1):5.
4. Aota N, Shiohara T. Viral connection between drug rashes and autoimmune diseases: how autoimmune responses are generated after resolution of drug rashes. *Autoimmun Rev.* 2009; 8: 488-94.
5. Naranjo C A, Busto U, Sellers E M, et al. A method for estimating the probability of adverse drug reactions. *Clin Pharmacol Ther.* 1981; 30:239-45.
6. Kardaun S H, Sekula P, Valeyrie-Allanore L, et al. Drug reaction with eosinophilia and systemic symptoms (DRESS): an original multisystem adverse drug reaction. Results from the prospective RegiSCAR study. *Br J Dermatol.* 2013; 169(5):1071-80.
7. Mallal S, Nolan D, Witt C, et al. Association between presence of HLA-B*5701, HLA-DR7, and HLA-DQ3 and hypersensitivity to HIV-1 reverse-transcriptase inhibitor abacavir. *Lancet.* 2002; 359:727-32.
8. Mallal S, Phillips E, Carosi G, et al. HLA-B*5701 screening for hypersensitivity to abacavir. *N Engl J Med.* 2008; 358:568-79.
9. Karnes J H, Shaffer C M, Bastarache L, et al. Comparison of HLA allelic imputation programs. *PLoS ONE.* 2017; 12(2):e0172444. doi:10.1371/journal.pone.0172444.
10. Keane N M, Roberts S G, Almeida C A, et al. High-avidity, high-IFNγ-producing CD8 T-cell responses following immune selection during HIV-1 infection. *Immunol Cell Biol.* 2012; 90(2):224-34.
11. Keane N M, Pavlos R K, McKinnon E, et al. HLA Class I restricted CD8+ and Class II restricted CD4+ T cells are implicated in the pathogenesis of nevirapine hypersensitivity. *AIDS.* 2014; 28(13):1891-901.
12. Trubiano J, Strautins K, Redwood A J, et al. The combined utility of ex vivo enzyme linked immunospot (ELISpot) and in vivo skin testing in patients with antibiotic-associated severe cutaneous adverse reactions. *J Allergy Clin Immunol Pract.* 2018; 6(4):1287-96.
13. Bordolo L, Kiefer F, Arnold K, Benkert P, Battey J, Schwede T. Protein structure homology modeling using SWISS-MODEL workspace. *Nat Protoc.* 2009; 4:1-13.
14. Emsley P, Lohkamp B, Scott W G, Cowtan K. Features and development of Coot. *Acta Crystallogr D Biol Crystallogr.* 2010; 66:486-501.
15. Adams P D, Afonine P V, Bunkoczi G, et al. PHENIX: a comprehensive Python-based system for macromolecular structure solution. *Acta Cryst.* 2010; D66:213-21.
16. Trott O, Olson A J. AutoDock Vina: improving the speed and accuracy of docking with a new scoring function, efficient optimization, and multithreading. *J Comput Chem.* 2010; 31(2):455-61.
17. Gragert L, Madbouly A, Freeman J, Maiers M. Six-locus high resolution HLA haplotype frequencies derived from mixed-resolution DNA typing for the entire US donor registry. *Hum Immunol.* 2013; 74(10):1313-20.
18. Rapin N, Hoof I, Lund O, Nielsen M MHC motif viewer. *Immunogenetics.* 2008; 60:759-65.
19. Chung W H, Hung S I, Hong H S, et al. Medical genetics: a marker for Stevens-Johnson syndrome. *Nature.* 2004; 428(6982):486.
20. Hetherington S, Hughes A R, Mosteller M, et al. Genetic variations in HLA-B region and hypersensitivity reactions to abacavir. *Lancet.* 2002; 359:1121-22.
21. Martin A M, Nolan D, Gaudieri S, et al. Predisposition to abacavir hypersensitivity conferred by HLA-B*5701 and a haplotypic Hsp70-Hom variant. *Proc Natl Acad Sci USA.* 2004; 101(12):4180-5.
22. Empedrad R, Darter A L, Earl H S, Gruchalla R S. Nonirritating intradermal skin test concentrations for commonly prescribed antibiotics. *J Allergy Clin Immunol.* 2003; 111(3):629-30.
23. Morito H, Ogawa K, Fukumoto T, et al. Increased ratio of FoxP3+ regulatory T cells/CD3+ T cells in skin lesions in drug induced hypersensitivity syndrome/drug rash with eosinophilia and systemic symptoms. *Cin Exp Dermatol.* 2014; 39(3):284-91.
24. Baden L A, Apovian C, Imber M J, Dover J S. Vancomycin-Induced Linear IgA Bullous Dermatosis. *Arch Dermatol.* 1988; 124(8):1186-88.
25. Minhas J S, Wickner P G, Long A A, Banerji A, Blumenthal K G. Immune-mediated reactions to vancomycin: A systematic case review and analysis. *Ann Allergy Asthma Immunol.* 2016; 116(6):544-53.
26. Ostrov D A, Grant B J, Pompeu Y A, et al. Drug hypersensitivity caused by alteration of the MHC-presented self-peptide repertoire. *Proc Natl Acad Sci USA.* 2012; 109:9959-64.
27. Illing P T, Vivian J P, Dudek N L, et al. Immune self-reactivity triggered by drug-modified HLA-peptide repertoire. *Nature.* 2012; 486(7404):554-8.

28. Redwood A J, Pavlos R K, White K D, Phillips E J: HLAs: Key Regulators of T-cell-Mediated Drug Hypersensitivity. HLA 2018, 91:3-16.
29. White K D, Chung W H, Hung S I, Mallal S, Phillips E J: Evolving Models of the Immunopathogenesis of T-cell-Mediated Drug Allergy: The Role of Host, Pathogens, and Drug Response. J Allergy Clin Immunol 2015, 136:219-234; quiz 235.
30. Paul S, Weiskopf D, Angelo M A, Sidney J, Peters B, Sette A: HLA Class I Alleles Are Associated with Peptide-Binding Repertoires of Different Size, Affinity, and Immunogenicity. J Immunol 2013, 191:5831-5839.
31. Konvinse K C, Trubiano J A, Pavlos R, James I, Shaffer C M, Bejan C A, Pilkinton M A, Rosenbach M, Zwerner J P, Williams K B, Jack Bourke J, Martinez P, Rwandamuriye F, Chopra A, Watson M, Mallal S A, Redwood A, White K D, Phillips E J: HLA-A*32:01 Is Strongly Associated with Vancomycin-Induced Drug Reaction with Eosinophilia and Systemic Symptoms. J Allergy Clin Immunol 2019.
32. Blumenthal K G, Peter J G, Trubiano J A, Phillips E J: Antibiotic Allergy. Lancet 2019, 393:183-198.
33. Husain Z, Reddy B Y, Schwartz R A: DRESS Syndrome: Part I. Clinical Perspectives. J Am Acad Dermatol 2013, 68:693 e691-614; quiz 706-698.
34. Pavlos R, Mallal S, Ostrov D, Buus S, Metushi I, Peters B, Phillips E: T Cell-Mediated Hypersensitivity Reactions to Drugs. Annu Rev Med 2015, 66:439-454.
35. Cacoub P, Musette P, Descamps V, Meyer O, Speirs C, Finzi L, Roujeau J C: The DRESS Syndrome: A Literature Review. Am J Med 2011, 124:588-597.
36. Carapito R, Radosavljevic M, Bahram S: Next-Generation Sequencing of the HLA Locus: Methods and Impacts on HLA Typing, Population Genetics and Disease Association Studies. Hum Immunol 2016, 77:1016-1023.
37. Sayer D, Whidborne R, Brestovac B, Trimboli F, Witt C, Christiansen F: HLA-Drb1 DNA Sequencing Based Typing: An Approach Suitable for High Throughput Typing Including Unrelated Bone Marrow Registry Donors. Tissue Antigens 2001, 57:46-54.
38. Roden D M, Pulley J M, Basford M A, Bernard G R, Clayton E W, Balser J R, Masys D R: Development of a Large-Scale De-Identified DNA Biobank to Enable Personalized Medicine. Clin Pharmacol Ther 2008, 84:362-369.
39. Ruiz-Villalba A, van Pelt-Verkuil E, Gunst Q D, Ruijter J M, van den Hoff M J: Amplification of Nonspecific Products in Quantitative Polymerase Chain Reactions (qPCR). Biomol Detect Quantif 2017, 14:7-18.
40. Ballantyne K N, van Oorschot R A, Mitchell R J: Locked Nucleic Acids in PCR Primers Increase Sensitivity and Performance. Genomics 2008, 91:301-305.
41. Cao K, Hollenbach J, Shi X J, Shi W X, Chopek M, Fernandez-Vina M A: Analysis of the Frequencies of HLA-a, B, and C Alleles and Haplotypes in the Five Major Ethnic Groups of the United States Reveals High Levels of Diversity in These Loci and Contrasting Distribution Patterns in These Populations. Hum Immunol 2001, 62:1009-1030.
42. Dunn P P: Human Leucocyte Antigen Typing: Techniques and Technology, a Critical Appraisal. Int J Immunogenet 2011, 38:463-473.
43. Nguyen D V, Vida C, Chu H C, Fulton R, Li J, Fernando S L: Validation of a Rapid, Robust, Inexpensive Screening Method for Detecting the HLA-B*58:01 Allele in the Prevention of Allopurinol-Induced Severe Cutaneous Adverse Reactions. Allergy Asthma Immunol Res 2017, 9:79-84.
44. Nguyen D V, Vidal C, Chu H C, Do N T, Tran T T, Le H T, Fulton R B, Li J, Fernando S L: Validation of a Novel Real-Time PCR Assay for Detection of HLA-B*15:02 Allele for Prevention of Carbamazepine—Induced Stevens-Johnson Syndrome/Toxic Epidermal Necrolysis in Individuals of Asian Ancestry. Hum Immunol 2016, 77:1140-1146.
45. Uchiyama K, Kubota F, Ariyoshi N, Matsumoto J, Ishii I, Kitada M: Development of a Simple Method for Detection of the HLA-A*31:01 Allele. Drug Metab Pharmacokinet 2013, 28:435-438.
46. Chen P, Lin J J, Lu C S, Ong C T, Hsieh P F, Yang C C, Tai C T, Wu S L, Lu C H, Hsu Y C, Yu H Y, Ro L S, Lu C T, Chu C C, Tsai J J, Su Y H, Lan S H, Sung S F, Lin S Y, Chuang H P, Huang L C, Chen Y J, Tsai P J, Liao H T, Lin Y H, Chen C H, Chung W H, Hung S I, Wu J Y, Chang C F, Chen L, Chen Y T, Shen C Y, Taiwan SJSC: Carbamazepine-Induced Toxic Effects and HLA-B*1502 Screening in Taiwan. N Engl J Med 2011, 364:1126-1133.
47. Hammond E, Mamotte C, Nolan D, Mallal S: HLA-B*5701 Typing: Evaluation of an Allele-Specific Polymerase Chain Reaction Melting Assay. Tissue Antigens 2007, 70:58-61.
48. Phillips E J, Mallal S A: Pharmacogenetics of Drug Hypersensitivity. Pharmacogenomics 2010, 11:973-987.
49. Ferrell P B, Jr., McLeod H L: Carbamazepine, HLA-B*1502 and Risk of Stevens-Johnson Syndrome and Toxic Epidermal Necrolysis: U S FDA Recommendations. Pharmacogenomics 2008, 9:1543-1546.
50. Van Bambeke F. Lipoglycopeptide Antibacterial Agents in Gram-Positive Infections: A Comparative Review. Drugs. 2015; 75(18):2073-95.
51. Kwon H S, Chang Y S, Jeong Y Y, Lee S M, Song W J, Kim H B, et al. A case of hypersensitivity syndrome to both vancomycin and teicoplanin. J Korean Med Sci. 2006; 21(6):1108-10.
52. Lye D, Athan E, O'Brien D. Teicoplanin hypersensitivity syndrome. Int J Antimicrob Agents. 2007; 29(4):476-8.
53. Miyazu D, Kodama N, Yamashita D, Tanaka H, Inoue S, Imakyure O, et al. DRESS Syndrome Caused by Cross-reactivity Between Vancomycin and Subsequent Teicoplanin Administration: A Case Report. Am J Case Rep. 2016; 17:625-31.
54. Ben Romdhane H, Chadli Z, Ben Fredj N, Chaabane A, Boughattas N A, Aouam K. Teicoplanin-induced DRESS syndrome: The importance of skin tests. Med Mal Infect. 2018; 48(4):291-3.
55. Ishizuka K T, Tran T K, Ayars A G, Chau A S, Chan J D. Graded Dalbavancin Challenge in a Patient with Severe Vancomycin Hypersensitivity Reaction. Clin Infect Dis. 2019.
56. Zhang T, Che D, Liu R, Han S, Wang N, Zhan Y, et al. Typical antimicrobials induce mast cell degranulation and anaphylactoid reactions via MRGPRX2 and its murine homologue MRGPRB2. Eur J Immunol. 2017; 47(11): 1949-58.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of detecting a human leukocyte antigen (HLA)-A*32:01 allele in a subject, comprising:
   (a) obtaining a biological sample from the subject;
   (b) detecting whether HLA-A*32:01 is present in the sample using a primer specific for a HLA-A*32 allele to determine whether the subject is at risk for developing or has vancomycin-induced drug reaction with eosinophilia and systemic symptoms (DRESS) when HLA-A*32:01 is present in the sample, wherein the primer specific for HLA-A*32 is HLA 32-88F (SEQ ID NO: 1).

2. The method of claim 1, wherein the subject has a bacterial infection.

3. The method of claim 2, wherein the bacteria is an antibiotic-resistant gram-positive bacteria.

4. The method of claim 1, wherein the biological sample is from a subject suspected of having DRESS.

5. The method of claim 4, wherein the subject is receiving combination antibiotic treatment that includes vancomycin.

6. The method of claim 5, wherein the subject is diagnosed as having vancomycin-induced DRESS when the presence of HLA-A*32:01 in the sample is detected.

7. The method of claim 6, further comprising administering to the diagnosed subject an antibiotic treatment that excludes vancomycin.

8. The method of claim 1, wherein the biological sample is from a subject in need of treatment with an antibiotic.

9. The method of claim 8, and further comprising identifying the subject as being at risk for developing vancomycin DRESS when the presence of HLA-A*32:01 in the sample is detected.

10. The method of claim 9, further comprising administering an antibiotic that is not vancomycin, teicoplanin, televancin, or a glycopeptide antibiotic to the identified subject.

11. The method of claim 9, further comprising administering dalbavancin to the identified subject.

12. The method of claim 1, wherein sequenced-based typing is conducted to determine whether HLA-A*32:01 is present in the sample.

13. The method of claim 1, wherein SNP2HLA is used to determine whether HLA-A*32:01 is present in the sample.

14. The method of claim 1, and further comprising using an IFN-γ Enzyme-Linked ImmuneSpot assay.

15. The method of claim 1, wherein a polymerase chain reaction assay is used to determine whether HLA-A*32:01 is present in the sample.

16. The method of claim 1, and further using a second primer specific for HLA-A*32 that is HLA032R2 (SEQ ID NO: 2).

17. A kit comprising a primer specific for HLA-A*32, including HLA-A*32 is HLA 32-88F (SEQ ID NO: 1) and HLA-A*32 that is HLA032R2 (SEQ ID NO: 2).

18. A method of identifying risk of developing vancomycin-induced drug reaction with eosinophilia and systemic symptoms (DRESS) in a subject, comprising:
  (a) obtaining a biological sample from the subject; and
  (b) detecting whether HLA-A*32:01 is present in the sample using a primer mix containing one or both of HLA 32-88F (SEQ ID NO: 1) and HLA032R2 (SEQ ID NO: 2).

19. A method of diagnosing vancomycin DRESS in a subject and treating the subject for a bacterial infection, comprising:
  (a) obtaining a biological sample from the subject;
  (b) detecting whether HLA-A*32:01 is present in the sample using a primer mix containing one or both of HLA 32-88F (SEQ ID NO: 1) and HLA032R2 (SEQ ID NO: 2);
  (c) diagnosing the subject with, or being at risk of developing, vancomycin DRESS when the presence of HLA-A*32:01 in the sample is detected; and
  (d) administering an antibiotic that is not vancomycin to the diagnosed subject.

* * * * *

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
gacgacacgc agttcgtgcg gtt                                                 23

<210> SEQ ID NO 2
<211> LENGTH: 17
<212> TYPE: DNA
<213> ORGANISM: Artificial Sequence
<220> FEATURE:
<223> OTHER INFORMATION: primer

<400> SEQUENCE: 2
gagcgcgatc cgcaggc                                                        17

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ttacccagag ccctatcgtt ct                                                  22

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gtctgcccat caccacctat t                                                   21
```